(12) United States Patent
Goldberg

(10) Patent No.: US 12,611,321 B2
(45) Date of Patent: Apr. 28, 2026

(54) DELIVERY APPARATUS HAVING NOSECONE WITH PIVOTABLE END PORTION

(71) Applicant: Edwards Lifesciences Corporation, Irvine, CA (US)

(72) Inventor: Eran Goldberg, Nesher (IL)

(73) Assignee: Edwards Lifesciences Corporation, Irvine, CA (US)

( * ) Notice: Subject to any disclaimer, the term of this patent is extended or adjusted under 35 U.S.C. 154(b) by 860 days.

(21) Appl. No.: 17/902,310

(22) Filed: Sep. 2, 2022

(65) Prior Publication Data

US 2022/0409410 A1    Dec. 29, 2022

Related U.S. Application Data

(63) Continuation of application No. PCT/US2021/020822, filed on Mar. 4, 2021.

(60) Provisional application No. 62/986,570, filed on Mar. 6, 2020.

(51) Int. Cl.
*A61F 2/95* (2013.01)
*A61F 2/24* (2006.01)
*A61F 2/958* (2013.01)

(52) U.S. Cl.
CPC .......... *A61F 2/9517* (2020.05); *A61F 2/2439* (2013.01); *A61F 2002/9583* (2013.01)

(58) Field of Classification Search
CPC .......... A61F 2/2427–2/2439; A61B 2017/003; A61M 25/0147; A61M 25/0067; A61M 25/0138
See application file for complete search history.

(56) References Cited

U.S. PATENT DOCUMENTS

| 3,409,013 A | 11/1968 | Berry |
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |

(Continued)

FOREIGN PATENT DOCUMENTS

| DE | 0144167 C | 9/1903 |
| DE | 2246526 A1 | 3/1973 |

(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.

(Continued)

*Primary Examiner* — Alvin J Stewart
(74) *Attorney, Agent, or Firm* — Klarquist Sparkman, LLP

(57) ABSTRACT

A delivery apparatus for an implantable medical device includes a handle, a shaft having a proximal end portion and a distal end portion, the proximal end portion being coupled to the handle, and a nosecone coupled to the distal end portion of the shaft. The nosecone includes a proximal end portion and a distal end portion pivotably coupled to the proximal end portion.

20 Claims, 11 Drawing Sheets

(56)                 References Cited

U.S. PATENT DOCUMENTS

| | | | |
|---|---|---|---|
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,441,216 A | 4/1984 | Ionescu et al. |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,820,299 A | 4/1989 | Philippe et al. |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely et al. |
| 5,554,185 A | 9/1996 | Block et al. |
| 5,558,644 A | 9/1996 | Boyd et al. |
| 5,571,175 A | 11/1996 | Vanney et al. |
| 5,584,803 A | 12/1996 | Stevens et al. |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,628,792 A | 5/1997 | Lentell |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein et al. |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler et al. |
| 5,855,602 A | 1/1999 | Angell |
| 5,925,063 A | 7/1999 | Khosravi |
| 5,957,949 A | 9/1999 | Leonhardt et al. |
| 6,027,525 A | 2/2000 | Suh et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasekaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian et al. |
| 6,302,906 B1 | 10/2001 | Goecoechea et al. |
| 6,350,277 B1 | 2/2002 | Kocur |
| 6,352,547 B1 | 3/2002 | Brown et al. |
| 6,425,916 B1 | 7/2002 | Garrison et al. |
| 6,440,764 B1 | 8/2002 | Focht et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle et al. |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely |
| 6,582,462 B1 | 6/2003 | Andersen et al. |
| 6,605,112 B1 | 8/2003 | Moll et al. |
| 6,652,578 B2 | 11/2003 | Bailey et al. |
| 6,689,123 B2 | 2/2004 | Pinchasik |
| 6,716,244 B2 | 4/2004 | Klaco |
| 6,730,118 B2 | 5/2004 | Spenser et al. |
| 6,733,525 B2 | 5/2004 | Yang et al. |
| 6,767,362 B2 | 7/2004 | Schreck |
| 6,769,161 B2 | 8/2004 | Brown et al. |
| 6,783,542 B2 | 8/2004 | Eidenschink |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 6,936,067 B2 | 8/2005 | Buchanan |
| 7,018,406 B2 | 3/2006 | Seguin et al. |
| 7,018,408 B2 | 3/2006 | Bailey et al. |
| 7,096,554 B2 | 8/2006 | Austin et al. |
| 7,225,518 B2 | 6/2007 | Eidenschink et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,563,280 B2 | 7/2009 | Anderson et al. |
| 7,585,321 B2 | 9/2009 | Cribier |
| 7,618,446 B2 | 11/2009 | Andersen et al. |
| 7,618,447 B2 | 11/2009 | Case et al. |
| 7,655,034 B2 | 2/2010 | Mitchell et al. |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,167,932 B2 | 5/2012 | Bourang |
| 8,291,570 B2 | 10/2012 | Eidenschink et al. |
| 8,449,606 B2 | 5/2013 | Eliasen et al. |
| 8,454,685 B2 | 6/2013 | Hariton et al. |

(56) References Cited

U.S. PATENT DOCUMENTS

| | | | |
|---|---|---|---|
| 8,652,203 B2 | 2/2014 | Quadri et al. | |
| 8,747,463 B2 | 6/2014 | Fogarty et al. | |
| 9,078,781 B2 | 7/2015 | Ryan et al. | |
| 10,646,340 B2* | 5/2020 | Manash | A61M 25/0138 |
| 11,224,509 B2 | 1/2022 | Dasi et al. | |
| 11,793,394 B2* | 10/2023 | Garbin | A61M 25/0084 |
| 2001/0021872 A1 | 9/2001 | Bailey et al. | |
| 2002/0026094 A1 | 2/2002 | Roth | |
| 2002/0032481 A1 | 3/2002 | Gabbay | |
| 2002/0138135 A1 | 9/2002 | Duerig et al. | |
| 2002/0173842 A1 | 11/2002 | Buchanan | |
| 2003/0050694 A1 | 3/2003 | Yang et al. | |
| 2003/0100939 A1 | 5/2003 | Yodfat et al. | |
| 2003/0158597 A1 | 8/2003 | Quiachon et al. | |
| 2003/0212454 A1 | 11/2003 | Scott et al. | |
| 2004/0039436 A1 | 2/2004 | Spenser et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0010285 A1 | 1/2005 | Lambrecht et al. | |
| 2005/0075725 A1 | 4/2005 | Rowe | |
| 2005/0075728 A1 | 4/2005 | Nguyen et al. | |
| 2005/0096736 A1 | 5/2005 | Osse et al. | |
| 2005/0188525 A1 | 9/2005 | Weber et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2006/0004469 A1 | 1/2006 | Sokel | |
| 2006/0025857 A1 | 2/2006 | Bergheim et al. | |
| 2006/0058872 A1 | 3/2006 | Salahieh et al. | |
| 2006/0074484 A1 | 4/2006 | Huber | |
| 2006/0149350 A1 | 7/2006 | Patel et al. | |
| 2006/0183383 A1 | 8/2006 | Asmus et al. | |
| 2006/0229719 A1 | 10/2006 | Marquez et al. | |
| 2006/0259137 A1 | 11/2006 | Artof et al. | |
| 2006/0271068 A1 | 11/2006 | Cao | |
| 2006/0287717 A1 | 12/2006 | Rowe et al. | |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0112422 A1 | 5/2007 | Dehdashtian | |
| 2007/0162102 A1 | 7/2007 | Ryan et al. | |
| 2007/0203503 A1 | 8/2007 | Salahieh et al. | |
| 2007/0203575 A1 | 8/2007 | Forster et al. | |
| 2007/0203576 A1 | 8/2007 | Lee et al. | |
| 2007/0213813 A1 | 9/2007 | Von Segesser et al. | |
| 2007/0233228 A1 | 10/2007 | Eberhardt et al. | |
| 2007/0260305 A1 | 11/2007 | Drews et al. | |
| 2007/0265700 A1 | 11/2007 | Eliasen et al. | |
| 2008/0114442 A1 | 5/2008 | Mitchell et al. | |
| 2008/0125853 A1 | 5/2008 | Bailey et al. | |
| 2008/0154355 A1 | 6/2008 | Benichou et al. | |
| 2008/0183271 A1 | 7/2008 | Frawley et al. | |
| 2008/0243245 A1 | 10/2008 | Thambar et al. | |
| 2008/0275537 A1 | 11/2008 | Limon | |
| 2009/0099554 A1* | 4/2009 | Forster | A61F 2/2427 |
| | | | 606/1 |
| 2009/0125118 A1 | 5/2009 | Gong | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0299452 A1 | 12/2009 | Eidenschink et al. | |
| 2009/0319037 A1 | 12/2009 | Rowe et al. | |
| 2010/0049313 A1 | 2/2010 | Alon et al. | |
| 2010/0099949 A1* | 4/2010 | Tilson | A61B 1/0055 |
| | | | 600/116 |
| 2010/0168844 A1 | 7/2010 | Toomes et al. | |
| 2010/0198347 A1 | 8/2010 | Zakay et al. | |
| 2010/0204781 A1 | 8/2010 | Alkhatib | |
| 2011/0015729 A1 | 1/2011 | Jimenez et al. | |
| 2011/0066224 A1 | 3/2011 | White | |
| 2011/0137397 A1 | 6/2011 | Chau et al. | |
| 2011/0218619 A1 | 9/2011 | Benichou et al. | |
| 2011/0319991 A1 | 12/2011 | Hariton et al. | |
| 2012/0089223 A1 | 4/2012 | Nguyen et al. | |
| 2012/0101571 A1 | 4/2012 | Thambar et al. | |
| 2012/0123529 A1 | 5/2012 | Levi et al. | |
| 2012/0259409 A1 | 10/2012 | Nguyen et al. | |
| 2013/0023985 A1 | 1/2013 | Khairkhahan et al. | |
| 2013/0046373 A1 | 2/2013 | Cartledge et al. | |
| 2013/0150956 A1 | 6/2013 | Yohanan et al. | |
| 2013/0166017 A1 | 6/2013 | Cartledge et al. | |
| 2013/0190857 A1 | 7/2013 | Mitra et al. | |
| 2013/0274873 A1 | 10/2013 | Delaloye et al. | |
| 2013/0297012 A1 | 11/2013 | Willard | |
| 2013/0310926 A1 | 11/2013 | Hariton | |
| 2013/0317598 A1 | 11/2013 | Rowe et al. | |
| 2013/0331929 A1 | 12/2013 | Mitra et al. | |
| 2014/0194981 A1 | 7/2014 | Menk et al. | |
| 2014/0200661 A1 | 7/2014 | Pintor et al. | |
| 2014/0209238 A1 | 7/2014 | Bonyuet et al. | |
| 2014/0222136 A1 | 8/2014 | Geist et al. | |
| 2014/0277417 A1 | 9/2014 | Schraut et al. | |
| 2014/0277419 A1 | 9/2014 | Garde et al. | |
| 2014/0277424 A1 | 9/2014 | Oslund | |
| 2014/0277563 A1 | 9/2014 | White | |
| 2014/0330372 A1 | 11/2014 | Weston et al. | |
| 2014/0343671 A1 | 11/2014 | Yohanan et al. | |
| 2014/0350667 A1 | 11/2014 | Braido et al. | |
| 2015/0073545 A1 | 3/2015 | Braido | |
| 2015/0073546 A1 | 3/2015 | Braido | |
| 2016/0136398 A1* | 5/2016 | Heilman | A61M 25/0108 |
| | | | 604/9 |
| 2018/0049873 A1* | 2/2018 | Manash | A61M 25/09 |
| 2018/0140323 A1* | 5/2018 | Foster | A61F 2/962 |
| 2019/0091021 A1* | 3/2019 | Morrissey | A61F 2/2427 |
| 2021/0236776 A1* | 8/2021 | Anderson | A61B 17/22 |
| 2022/0265127 A1* | 8/2022 | Tilson | A61B 1/0051 |
| 2022/0347434 A1* | 11/2022 | Saleh | A61M 25/0138 |
| 2023/0016149 A1* | 1/2023 | Griswold | A61M 25/0147 |
| 2023/0078736 A1* | 3/2023 | Brauon | A61M 25/0136 |
| | | | 604/95.01 |
| 2023/0201531 A1* | 6/2023 | Ramanathan | A61M 25/0102 |
| | | | 604/525 |
| 2023/0355385 A1* | 11/2023 | Shally | A61F 2/9517 |
| 2023/0405270 A1* | 12/2023 | Mcguinn | A61F 2/958 |
| 2024/0024105 A1* | 1/2024 | McDermott | A61F 2/2427 |
| 2024/0299164 A1* | 9/2024 | Lopez | A61F 2/2439 |
| 2024/0316318 A1* | 9/2024 | Shaolian | A61M 25/0136 |
| 2025/0195827 A1* | 6/2025 | Schabert | A61M 25/09 |

FOREIGN PATENT DOCUMENTS

| | | | |
|---|---|---|---|
| DE | 19532846 A1 | 3/1997 | |
| DE | 19546692 A1 | 6/1997 | |
| DE | 19857887 A1 | 7/2000 | |
| DE | 19907646 A1 | 8/2000 | |
| DE | 10049812 A1 | 4/2002 | |
| DE | 10049813 C1 | 4/2002 | |
| DE | 10049814 A1 | 4/2002 | |
| DE | 10049815 A1 | 4/2002 | |
| EP | 0103546 A1 | 3/1984 | |
| EP | 0850607 A1 | 7/1998 | |
| EP | 1057460 A1 | 12/2000 | |
| EP | 1088529 A2 | 4/2001 | |
| EP | 1570809 A1 | 9/2005 | |
| EP | 3391857 A1 | 10/2018 | |
| FR | 2788217 A1 | 7/2000 | |
| FR | 2815844 A1 | 5/2002 | |
| GB | 2056023 A | 3/1981 | |
| SU | 1271508 A1 | 11/1986 | |
| WO | 9117720 A1 | 11/1991 | |
| WO | 9217118 A1 | 10/1992 | |
| WO | 9301768 A1 | 2/1993 | |
| WO | 9724080 A1 | 7/1997 | |
| WO | 9829057 A1 | 7/1998 | |
| WO | 9930646 A1 | 6/1999 | |
| WO | 9933414 A1 | 7/1999 | |
| WO | 9940964 A1 | 8/1999 | |
| WO | 9947075 A1 | 9/1999 | |
| WO | 0018333 A1 | 4/2000 | |
| WO | 0041652 A1 | 7/2000 | |
| WO | 0047139 A1 | 8/2000 | |
| WO | 0135878 A2 | 5/2001 | |

(56) References Cited

FOREIGN PATENT DOCUMENTS

| WO | 0149213 | A2 | 7/2001 | |
| WO | 0154624 | A1 | 8/2001 | |
| WO | 0154625 | A1 | 8/2001 | |
| WO | 0162189 | A1 | 8/2001 | |
| WO | 0164137 | A1 | 9/2001 | |
| WO | 0176510 | A2 | 10/2001 | |
| WO | 0222054 | A1 | 3/2002 | |
| WO | 0236048 | A1 | 5/2002 | |
| WO | 0241789 | A2 | 5/2002 | |
| WO | 0243620 | A1 | 6/2002 | |
| WO | 0247575 | A2 | 6/2002 | |
| WO | 0249540 | A2 | 6/2002 | |
| WO | 03047468 | A1 | 6/2003 | |
| WO | 2005034812 | A1 | 4/2005 | |
| WO | 2005055883 | A1 | 6/2005 | |
| WO | 2005084595 | A1 | 9/2005 | |
| WO | 2005102015 | A2 | 11/2005 | |
| WO | 2006014233 | A2 | 2/2006 | |
| WO | 2006032051 | A2 | 3/2006 | |
| WO | 2006034008 | A2 | 3/2006 | |
| WO | 2006111391 | A1 | 10/2006 | |
| WO | 2006127089 | A1 | 11/2006 | |
| WO | 2006138173 | A2 | 12/2006 | |
| WO | 2007047488 | A2 | 4/2007 | |
| WO | 2007067942 | A1 | 6/2007 | |
| WO | WO-2007084724 | A2 | 7/2007 | |
| WO | 2007097983 | A2 | 8/2007 | |
| WO | 2008005405 | A2 | 1/2008 | |
| WO | 2008015257 | A2 | 2/2008 | |
| WO | 2008035337 | A2 | 3/2008 | |
| WO | 2008091515 | A2 | 7/2008 | |
| WO | 2008147964 | A1 | 12/2008 | |
| WO | 2008150529 | A1 | 12/2008 | |
| WO | 2009033469 | A1 | 3/2009 | |
| WO | 2009042196 | A2 | 4/2009 | |
| WO | 2009053497 | A1 | 4/2009 | |
| WO | 2009061389 | A2 | 5/2009 | |
| WO | 2009094188 | A2 | 7/2009 | |
| WO | WO-2009091509 | A1 | 7/2009 | |
| WO | 2009116041 | A2 | 9/2009 | |
| WO | 2009149462 | A2 | 12/2009 | |
| WO | 2010011699 | A2 | 1/2010 | |
| WO | 2010121076 | A2 | 10/2010 | |
| WO | 2013106585 | A1 | 7/2013 | |
| WO | 2015085218 | A1 | 6/2015 | |
| WO | WO-2018023052 | A1 * | 2/2018 | ........ A61M 25/0147 |
| WO | WO-2023091422 | A1 * | 5/2023 | ............ A61F 2/243 |

OTHER PUBLICATIONS

H.R. Andersen "History of Percutaneous Aortic Valve Prosthesis," Herz No. 34. pp. 343-346. 2009.

Pavcnik, et al. "Development and initial Experimental Evaluation of a Prosthetic Aortic Valve for Transcatheter Placement," Cardiovascular Radiology, vol. 183, No. 1. pp. 151-154. 1992.

Bailey, S. "Percutaneous Expandable Prosthetic Valves," Textbook of Interventional Cardiology vol. 2, 2nd Ed. pp. 1268-1276. 1994.

Al-Khaja, et al. "Eleven Years' Experience with Carpentier-Edwards Biological Valves in Relation to Survival and Complications," European Journal of Cardiothoracic Surgery, vol. 3. pp. 305-311. 1989.

Ross, "Aortic Valve Surgery," At a meeting of the Council on Aug. 4, 1966. pp. 192-197.

Sabbah, et al. "Mechanical Factors in the Degeneration of Porcine Bioprosthetic Valves: An Overview," Journal of Cardiac Surgery, vol. 4, No. 4. pp. 302-309. 1989.

Wheatley, "Valve Prostheses," Operative Surgery, 4th ed. pp. 415-424. 1986.

Uchida, "Modifications of Gianturco Expandable Wire Stents," American Journal of Roentgenology, vol. 150. pp. 1185-1187. 1986.

Walther T, Dehdashtian MM, Khanna R, Young E, Goldbrunner PJ, Lee W. Trans-catheter valve-in-valve implantation: in vitro hydrodynamic performance of the SAPIEN+cloth trans-catheter heart valve in the Carpentier-Edwards Perimount valves. Eur J Cardiothorac Surg. 2011;40(5):1120-6. Epub Apr. 7, 2011.

* cited by examiner

116

118

108

114

132

136

126

140

142

138

144

148

150

146

DELIVERY APPARATUS HAVING NOSECONE WITH PIVOTABLE END PORTION

CROSS-REFERENCED TO RELATED APPLICATION

The present application is a continuation of PCT Application No. PCT/US2021/020822, entitled "DELIVERY APPARATUS HAVING NOSECONE WITH A BALL JOINT," filed Mar. 4, 2021, which claims the benefit of U.S. Provisional Application No. 62/986,570, entitled "DELIVERY APPARATUS HAVING NOSECONE WITH A BALL JOINT," filed Mar. 6, 2020, wherein each of the above-referenced applications is incorporated herein by reference in its entirety.

FIELD

The present disclosure concerns embodiments of prosthetic valve delivery assemblies and related methods.

BACKGROUND

Endovascular delivery devices are used in various procedures to deliver prosthetic medical devices or instruments to locations inside the body that are not readily accessible by surgery or where access without surgery is desirable. Access to a target location inside the body can be achieved by inserting and guiding the delivery device through a pathway or lumen in the body, including, but not limited to, a blood vessel, an esophagus, a trachea, any portion of the gastro-intestinal tract, a lymphatic vessel, to name a few. In one specific example, a prosthetic heart valve can be mounted in a crimped state on the distal end of a delivery device and advanced through the patient's vasculature (e.g., through a femoral artery and the aorta) until the prosthetic valve reaches the implantation site in the heart. The prosthetic valve is then expanded to its functional size, for example, by inflating a balloon on which the prosthetic valve is mounted, or by deploying the prosthetic valve from a sheath of the delivery device so that the prosthetic valve can self-expand to its functional size. Despite the recent advancements in percutaneous valve technology, there remains a need for improved systems and methods for delivery of such valves.

SUMMARY

Described herein are prosthetic valve delivery assemblies and related methods, which can be used to deliver a prosthetic valve to a location within a body of a subject. In some implementations, the prosthetic valve delivery assemblies can be used to deliver a medical device through the vasculature, such as to a heart of the subject.

In one representative embodiment, a delivery apparatus for an implantable medical device is provided. The delivery apparatus includes a handle, a shaft, and a nosecone. The shaft has a proximal end portion and a distal end portion, the proximal end portion being coupled to the handle. The nosecone is coupled to the distal end portion of the shaft and includes a proximal end portion and a distal end portion pivotably coupled to the proximal end portion.

In another representative embodiment, a delivery apparatus includes a handle, a first shaft, a second shaft extending over the first shaft, and a nosecone. The first shaft has a proximal end portion and a distal end portion, the proximal end portion being coupled to the handle, and the second shaft includes a delivery capsule along a distal end thereof. The nosecone is coupled to the distal end portion of the first shaft and has a proximal end portion and a distal end portion pivotably coupled to the proximal end portion by a ball and socket joint. The ball and socket joint includes a ball disposed in a socket, where one of the proximal end portion and the distal end portion includes the ball and the other of the proximal end portion and distal end portion includes the socket. The proximal end portion of the nosecone includes a first lumen and the distal end portion of the nosecone includes a second lumen. The first lumen and the second lumen are sized to receive a guidewire therethrough, and the distal end portion of the first shaft extends into the first lumen of the proximal end portion. The delivery capsule is configured to retain a medical implant in a radially collapsed state for delivery into a patient, where a distal end section of the delivery capsule is sized to extend over the proximal end portion of the nosecone.

In another representative embodiment, a delivery apparatus includes a handle, a shaft a nosecone. The shaft has a proximal end portion and a distal end portion, the proximal end portion being coupled to the handle. The nosecone is coupled to the distal end portion of the shaft, where the nosecone includes a proximal end portion and a distal end portion pivotably coupled to the proximal end portion by a ball and socket joint. The ball and socket joint includes a ball disposed in a socket, where the proximal end portion includes the socket and the distal end portion includes the ball.

In another representative embodiment, a delivery apparatus includes a handle, a shaft, and a nosecone. The shaft has a proximal end portion and a distal end portion, the proximal end portion being coupled to the handle. The nosecone is coupled to the distal end portion of the shaft and includes a proximal end portion, a distal end portion coupled to the proximal end portion, and a coupling means for coupling the distal end portion and the proximal end portion. The coupling means permits pivoting movement of the distal end portion relative to the proximal end portion.

In one representative embodiment, an implantable medical device delivery assembly is provided. The delivery assembly includes delivery apparatus having a handle, a nosecone, an expandable implantable medical device, and a shaft having a proximal end portion and a distal end portion. The proximal end portion of the shaft is coupled to the handle and the distal end portion is coupled to the nosecone. The expandable implantable medical device is mounted in a radial configuration around the distal end portion of the shaft. The nosecone includes a proximal end portion and a distal end portion pivotably coupled to the proximal end portion.

In another representative embodiment, a delivery assembly includes a delivery apparatus having a handle, a nosecone, a shaft having a proximal end portion and a distal end portion, and an expandable implantable medical device. The nosecone is coupled to the distal end portion and the proximal end portion is coupled to the handle. The expandable implantable medical device is mounted in a radial configuration around the distal end portion of the shaft. The nosecone includes a proximal end portion and a distal end portion pivotably coupled to the proximal end portion by a ball and socket joint. One of the proximal end portion and the distal end portion includes the ball and the other of the proximal end portion and distal end portion includes the socket.

In another representative embodiment, a delivery assembly includes a delivery apparatus having a handle, a nosecone, a first shaft, a second shaft extending over the first shaft, and an expandable implantable medical device. The first shaft has a distal end portion and a proximal end portion coupled to the handle. The second shaft includes a delivery capsule along a distal end section thereof, and the nosecone has a proximal end portion and a distal end portion pivotably coupled to the proximal end portion. The expandable implantable medical device is mounted in a radially compressed configuration around the distal end portion of the first shaft and within the delivery capsule of the second shaft. The distal end portion and the proximal end portion of the nosecone are pivotably coupled by a ball and socket joint including a ball disposed in a socket. The distal end portion comprises the ball and the proximal end portion includes the socket. A distal end section of the delivery capsule is sized to extend over the proximal end portion of the nosecone.

In one representative embodiment, a method for delivering an implantable medical device is provided. The method can include advancing an expandable implantable medical device mounted in a radially compressed configuration around a distal end portion of a shaft of a delivery apparatus into a native lumen of a patient such that at least a distal end portion of a nosecone of the delivery apparatus contacts a vasculature wall of the patient. The contact between the nosecone and the vasculature wall causes the distal end portion of the nosecone to pivot relative to a proximal end portion of the nosecone. In some embodiments, the contact between the nosecone and the vasculature wall causes the distal end portion of the nosecone to rotate relative to the proximal end portion of the nosecone.

In one representative embodiment, a method for implanting a prosthetic valve into an aortic annulus of a patient is provided. The method includes advancing an expandable prosthetic valve and a distal end portion of a shaft of a delivery apparatus into an aorta of the patient, wherein the prosthetic valve is mounted in a radially compressed configuration around the distal end portion of the shaft, such that at least a distal end portion of a nosecone of the delivery apparatus contacts a wall of the aorta, wherein of the distal end portion of the nosecone is pivotably coupled to a proximal end portion of the nosecone, wherein the proximal end portion is coupled to the distal end portion of the shaft; wherein contact between the nosecone and the wall of the aorta causes the distal end portion of the nosecone to pivot relative to the proximal end portion of the nosecone, the distal end portion of the shaft, and the prosthetic valve; inserting the distal end portion of the shaft into an aortic annulus of the patient such that the nosecone extends through the aortic annulus and into a left ventricle of the patient; and expanding the prosthetic valve from a radially compressed state to a radially expanded state within the aortic annulus.

In another representative embodiment, a delivery apparatus for an implantable medical device includes a handle, a first shaft, a second shaft extending over the first shaft, and a nosecone coupled to the distal end portion of the first shaft. The first shaft includes a proximal end portion and a distal end portion, the proximal end portion being coupled to the handle. The second shaft includes a delivery capsule along a distal end thereof. The nosecone includes a proximal end portion, an intermediate portion pivotably coupled to the proximal end portion by a first ball and socket joint, and a distal end portion pivotably coupled to the intermediate portion by a second ball and socket joint. Each ball and socket joint include a ball disposed in a socket.

In one representative embodiment, a delivery apparatus for an implantable medical device includes a handle, a shaft having a proximal end portion and a distal end portion, the proximal end portion being coupled to the handle, and a nosecone coupled to the distal end portion of the shaft. The nosecone includes a proximal end portion and a distal end portion pivotably coupled to the proximal end portion by a plurality of ball and socket joints.

The various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosure will become more apparent from the following detailed description, claims, and accompanying figures.

DETAILED DESCRIPTION

General Considerations

Figure 1:
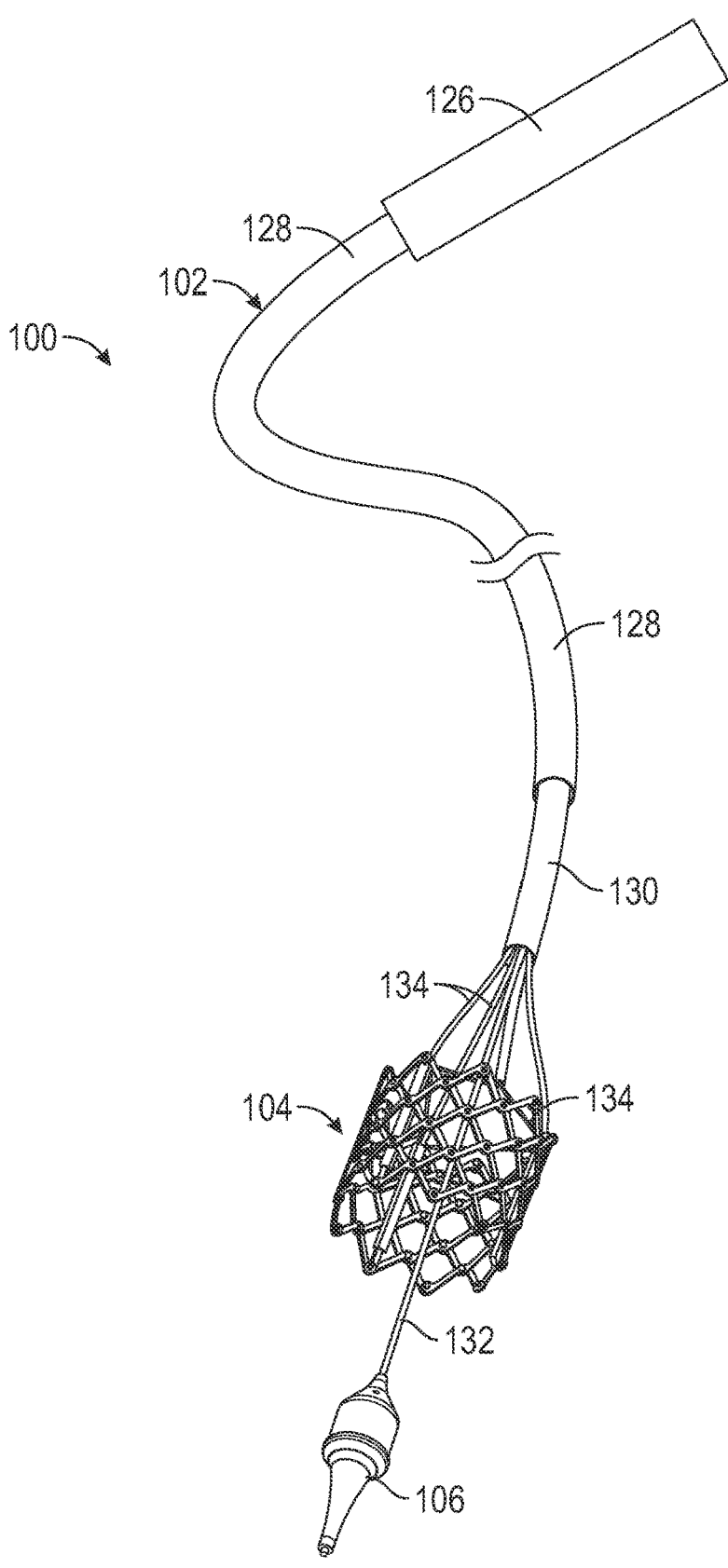
FIG. 1 is a perspective view of a delivery assembly comprising a mechanically-expandable prosthetic heart valve and a delivery apparatus.

It should be understood that the disclosed embodiments can be adapted for delivering and implanting prosthetic heart valves in any of the native annuluses of the heart (e.g., the aortic, pulmonary, mitral, and tricuspid annuluses), and can be used with any of the various delivery devices for delivering the prosthetic valve using any of a number of delivery approaches (e.g., retrograde, antegrade, transseptal, transseptal, transventricular, transatrial, etc.). Although the embodiments of delivery apparatuses disclosed herein are described in the context of being to implant a prosthetic heart valve, the delivery apparatuses can be used to deliver and implant any of various medical implants within the body, including, but not limited to, venous valves, stents, grafts, heart valve repair devices, etc.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not excluded the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while the distal motion of the device is motion of the device away from the user and toward the implantation site (e.g., into the patient's body). The term "longitudinal" and "axial" refer to an axis extending in the proximal and distal directions, unless otherwise expressly defined.

Exemplary Embodiments

Described herein are delivery apparatus and methods for implanting prosthetic heart valves, or other expandable medical devices. The disclosed delivery apparatus and methods can, for example, help to reduce the axial force needed to advance a delivery device around a vasculature arch. The reduction in the axial force can lower the risk of gap formation between the nosecone and the delivery capsule during implantation. The disclosed delivery apparatus and methods can also provide increased bendability in the nosecone to reduce the frictional forces between the nosecone and the guide wire and/or surrounding native vasculature wall. The delivery apparatus and the nosecone disclosed herein can also have a rigid section with an overall length shorter than that of the rigid sections of other standard delivery systems.

FIG. 1 shows a delivery assembly 100, according to one embodiment. In the illustrated embodiment, the delivery assembly 100 comprises a prosthetic heart valve 104 and a delivery apparatus 102 comprising a nosecone 106. The prosthetic valve can be configured to replace a native heart valve (e.g., aortic, mitral, pulmonary, and/or tricuspid valves). As shown, the prosthetic valve 104 can be releasably coupled to a distal end portion of the delivery apparatus 102. The delivery apparatus 102 and the nosecone 106 coupled to the distal end portion of the delivery apparatus 102 can be used to deliver and implant the prosthetic valve 104 in the native heart valve of a patient (e.g., shown in FIGS. 15 and 16). Additional details regarding the prosthetic valve 104, the delivery apparatus 102, and the nosecone 106 are provided below.

Figure 2:
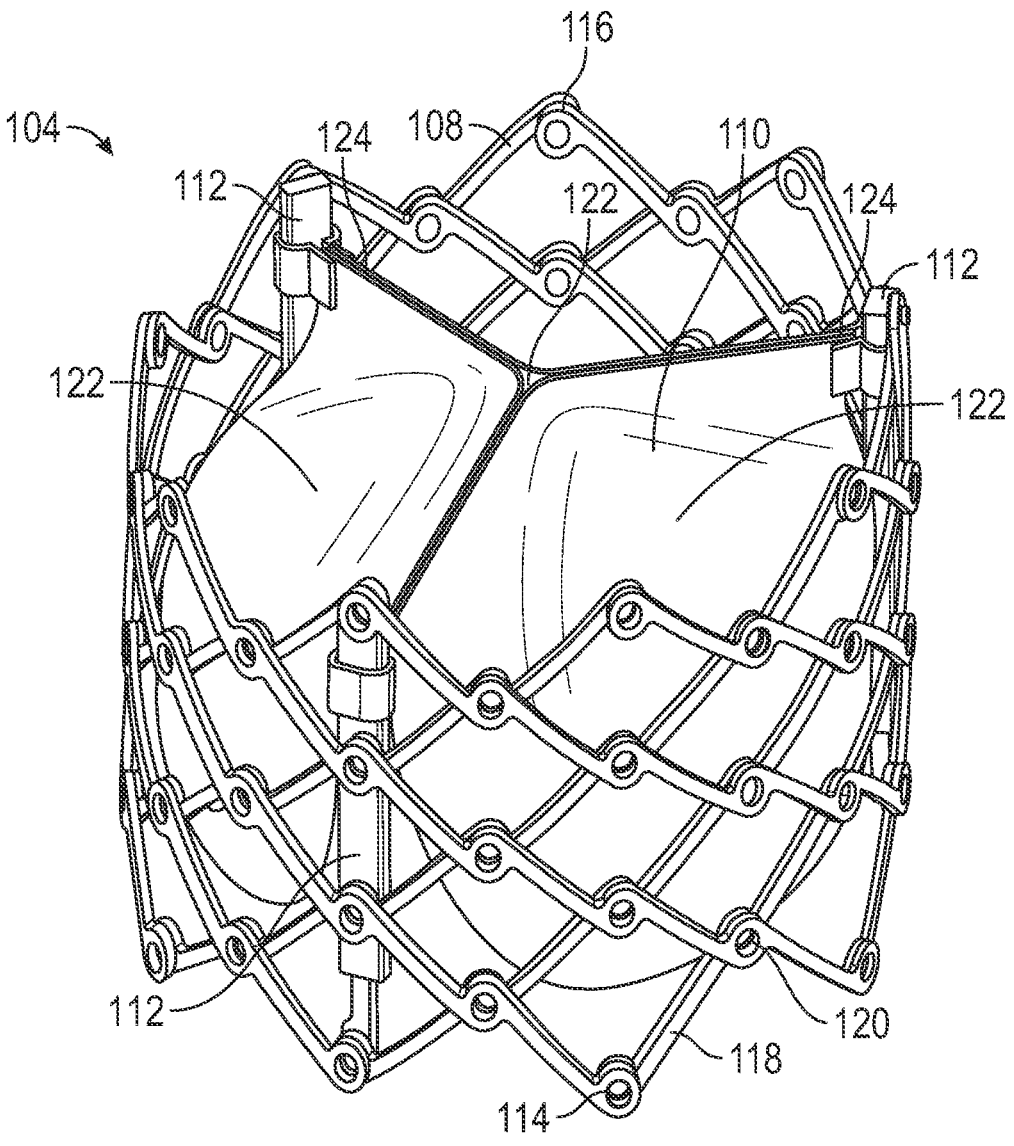
FIG. 2 is a perspective view of the prosthetic heart valve.

FIG. 2 shows the prosthetic valve 104, which is a mechanically-expandable heart valve in the illustrated embodiment. In other embodiments, the delivery apparatus 102 can be used to deliver and implant a balloon-expandable heart or a self-expandable heart valve. If used to deliver a balloon-expandable heart valve, the delivery apparatus 102 can include an inflatable balloon along a distal end portion thereof to expand the heart valve to its functional size, as known in the art. If used to deliver a self-expandable heart valve, the heart valve can be retained in a radially collapsed state within a sheath or capsule (e.g., capsule 186) for delivery into the body and can self-expand to its functional size by deploying the heart valve from the sheath, as known in the art.

As shown, for example, the prosthetic valve 104 can comprise three main components: a frame 108, a valve structure 110, and commissure members 112 (e.g., three actuators in the illustrated embodiment). The frame 108 (which can also be referred to as "a stent" or "a support structure") can be configured for supporting the valve structure 110 and for securing the prosthetic valve 104 within a native heart valve. The valve structure 110 is coupled to the frame 108 and/or to the commissure members 112. The valve structure 110 is configured to allow blood flow through the prosthetic valve 104 in one direction (i.e., antegrade) and to restrict blood flow through the prosthetic valve 104 in the opposite direction (i.e., retrograde). The commissure members 112 are coupled to the frame 108 and can be configured (e.g., as actuators) to adjust expansion of the frame 108 to a plurality of configurations including one or more functional or expanded configurations (e.g., FIG. 2), one or more delivery or compressed configurations (e.g., FIG. 3), and/or one or more intermediate configurations between the functional and delivery configurations. It should be noted that the valve structure 110 of the prosthetic valve 104 is not shown in FIGS. 1 and 3 for the purpose of illustration.

Referring to FIG. 2, the frame 108 of the prosthetic valve 104 has a first end 114 and a second end 116. In the illustrated embodiment, the first end 114 of the frame 108 is an inflow end and the second end 116 of the frame 108 is an outflow end. In other embodiments, the first end 114 of the frame 108 can be the outflow end and the second end 116 of the frame 108 can be the inflow end.

The frame 108 can also be made of any suitable materials, including biocompatible metals and/or biocompatible polymers. Exemplary biocompatible metals from which the frame can be formed include stainless steel, cobalt chromium alloy, and/or nickel titanium alloy (which can also be referred to as "NiTi" or "nitinol").

Figure 3:
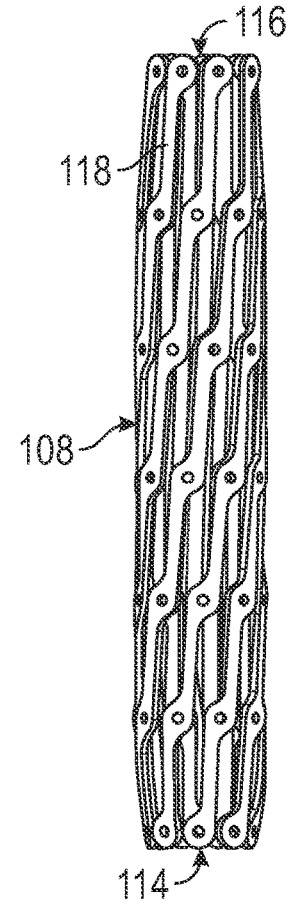
FIG. 3 is a side view of the bare frame of the prosthetic heart valve in a radially compressed configuration.

Still referring to FIG. 2, the frame 108 includes a plurality of interconnected struts 118 arranged in a lattice-type pattern. In FIG. 2, the frame 108 of the prosthetic valve 104 is in a radially expanded configuration, which results in the struts 118 of the frame 108 extending diagonally relative to a longitudinal axis of the prosthetic valve 104. In other configurations, the struts 118 of the frame 108 can be offset by a different amount than the amount depicted in FIG. 2. For example, FIG. 3 shows the frame 108 of the prosthetic valve 104 in a radially compressed configuration. In this configuration, the struts 118 of the frame 108 extend parallel (or at least substantially parallel) to the longitudinal axis of the prosthetic valve 104.

To facilitate movement between the expanded and compressed configurations, the struts 118 of the frame 108 are pivotably coupled to one another at one or more pivot joints along the length of each strut. For example, each of the struts 118 can be formed with apertures 120 at opposing ends and along the length of the strut. The frame 108 comprises hinges at the locations where struts 118 overlap and are pivotably coupled together via fasteners such as rivets or pins that extend through the apertures 120 of the struts 118. The hinges allow the struts 118 to pivot relative to one another as the frame 108 moves between the radially expanded and the radially compressed configurations, such as during assembly, preparation, and/or implantation of the prosthetic valve 104.

In some embodiments, the frame 108 can be constructed by forming individual components (e.g., the struts 118 and pins of the frame 108) and then mechanically assembling and coupling the individual components together. In other embodiments, the struts are not coupled to each other with respective hinges but are otherwise pivotable or bendable relative to each other to permit radial expansion and contraction of the frame. For example, a frame can be formed (e.g., via laser cutting, electroforming or physical vapor deposition) from a single piece of material (e.g., a metal tube). Further details regarding the construction of frames and prosthetic valves are described in U.S. Publication Nos. 2018/0153689, 2018/0344456, and 2019/0060057, U.S. Application No. 62/869,948, and International Application No. PCT/US2019/056865, which are incorporated by reference herein. Additional examples of expandable prosthetic valves that can be used with the delivery apparatus disclosed herein are described in U S. Publication Nos. 2015/0135506 and 2014/0296962, which are incorporated by reference herein.

Referring still to FIG. 2, the valve structure 110 of the prosthetic valve 104 is coupled to the frame 108. The valve structure 110 is configured to allow blood flow through the prosthetic valve 104 from the inflow end 114 to the outflow end 116 and to restrict blood from through the prosthetic valve 104 from the outflow end 116 to the inflow end 114. The valve structure 110 can include, for example, a leaflet assembly comprising one or more leaflets 122 (e.g., the three leaflets in the illustrated embodiment).

The leaflets 122 of the prosthetic valve 104 can be made of a flexible material. For example, the leaflets 122 of the leaflet assembly can be made from in whole or part, biological material, bio-compatible synthetic materials, or other such materials. Suitable biological material can include, for example, bovine pericardium (or pericardium from other sources).

The leaflets 122 can be arranged to form commissures 124 (e.g., pairs of adjacent leaflets), which can, for example, be mounted to respective commissure members 112. Further details regarding prosthetic heart valves, including the manner in which the valve structure 110 can be coupled to the frame 108 of the prosthetic valve 104, can be found in U.S. Pat. Nos. 6,730,118, 7,393,360, 7,510,575, 7,993,394, and 8,652,202, and U.S. Publication No. 2018/0325665, which are incorporated by reference herein.

The valve structure 110 can be coupled to the commissure members 112, which, for example, can be configured for actuation. As shown in FIG. 2, the commissure members 112 are mounted to and spaced circumferentially around the inner surface of the frame 108. The commissure members 112 are configured to, among other things, radially expand and/or radially compress the frame 108. For this reason, the commissure members 112 can also be referred to as "expansion mechanisms." The commissure members 112 are also configured to lock the frame 108 at a desired expanded configuration. Accordingly, the commissure members 112 can be referred to as "lockers" or "locking mechanisms." Each of the commissure members 112 can be configured to form a releasable connection with one or more respective actuation shafts of a delivery apparatus. Additional details regarding a valve structure coupled to a prosthetic valve comprising one or more actuators and a corresponding delivery apparatus can be found, for example, in U.S. Application No. 62/945,039 and in U.S. Application No. 62/869,948, which are incorporated by reference herein.

While the illustrated embodiment of FIG. 2 includes three commissure members 112 (e.g., actuators), various prosthetic valves and/or expansion mechanisms can be used with the delivery apparatus disclosed herein. For example, other embodiments can include various prosthetic valves that are self-expandable and/or mechanically expandable, such as those prosthetic valves incorporated by reference herein, or can be used in conjunction with any various expandable mechanisms such as, for example, inflatable devices, actuators, biasing members, etc.

Although not shown, the prosthetic valve 104 can also include one or more skirts or sealing members. For example, the prosthetic valve 104 can include an inner skirt mounted on the inner surface of the frame 108. The inner skirt can function as a sealing member to prevent or decrease perivalvular leakage, to anchor the leaflets 122 to the frame 108, and/or to protect the leaflets 122 against damage caused by contact with the frame 108 during crimping and during working cycles of the prosthetic valve 104. The prosthetic valve 104 can also include an outer skirt mounted on the outer surface of the frame 108. The outer skirt can function as a sealing member for the prosthetic valve 104 by sealing against the tissue of the native valve annulus and thus reducing paravalvular leakage around the prosthetic valve. The inner and outer skirts can be formed from any of various suitable biocompatible materials, including any of various synthetic materials (e.g., PET) or natural tissue (e.g., pericardial tissue). The inner and outer skirts can be mounted to the frame using sutures, an adhesive, welding, and/or other means for attaching the skirts to the frame.

Figure 4:
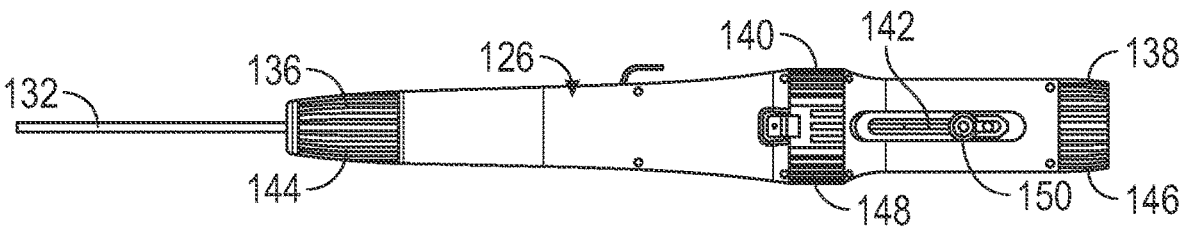
FIG. 4 is a side view of a proximal end portion of the delivery apparatus.
Figure 5:
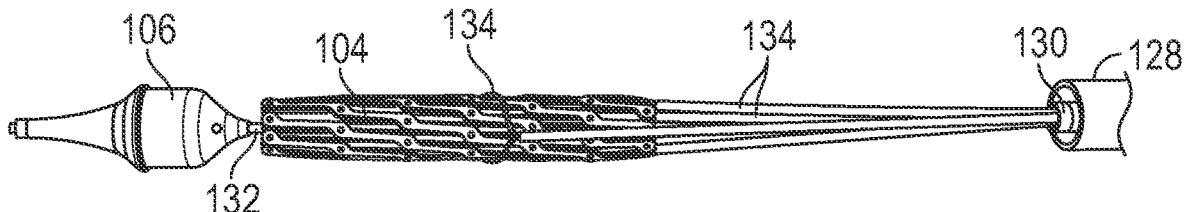
FIG. 5 is a side view of a nosecone coupled to a distal end portion of the delivery apparatus showing the delivery capsule retracted relative to the nosecone.
Figure 6:
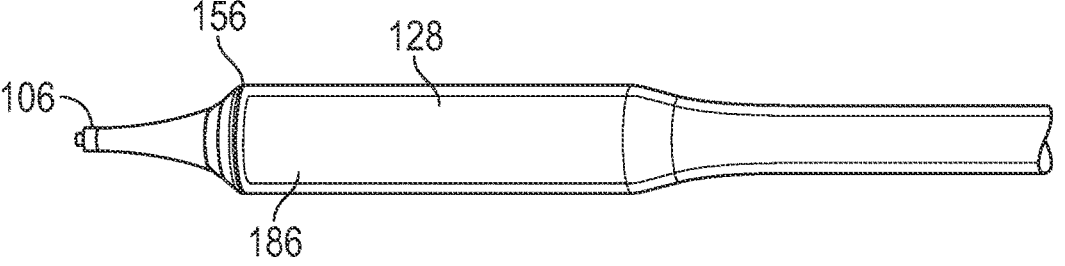
FIG. 6 is another side view of the nosecone coupled to a distal end portion of the delivery apparatus showing the delivery capsule extending partially over the nosecone.

FIGS. 4-6 show the delivery apparatus 102 and its components, which can also be referred to as a "valve catheter" or a "delivery catheter." As shown, the delivery apparatus 102 comprises a handle 126, a first shaft 128, second shaft 130, a nosecone shaft 132, a nosecone 106, and expansion (or alternatively compression) components 134 (e.g., support sleeves, actuation shafts, recompression shaft, etc.).

The handle 126 is configured for manipulating the shafts and sleeves relative to each other. The prosthetic heart valve 104 can be releasably coupled to the distal end portion of the delivery apparatus 102 (e.g., FIGS. 5 and 16), and the delivery apparatus 102 can be used for positioning the prosthetic valve 104, and/or for expanding, compressing, and locking the prosthetic valve 104 in a desired radially expanded configuration.

The handle 126 of the delivery apparatus 102 comprises one or more mechanisms configured to move the shafts and sleeves relative to each other. For example, as shown in FIG. 4, the handle 126 comprises a first mechanism 136, a second mechanism 138, a third mechanism 140, and/or a fourth mechanism 142.

The first mechanism 136 of the handle 126 is coupled to the first and second shafts 128, 130 and is configured to move the first and second shafts 128, 130 axially relative to each other. As further explained below, the first mechanism 136 of the handle 126 can be used to deploy the prosthetic valve 104 from the delivery capsule of the first shaft 128. As such, the first mechanism 136 can be referred to as a "deployment mechanism."

In the illustrated embodiment, the first mechanism 136 includes a first knob 144 configured for actuating the first mechanism 136. Although not shown, in other embodiments, the first mechanism 136 can comprise various other types of actuators configured for actuating the first mechanism 136, such as buttons, switches, etc. The first mechanism 136 can also include one or more other non-illustrated components (such as electric motors, rotatable shafts, drive screws, gear assemblies, etc.) configured to facilitate and/or restrict relative axial movement between the first and second shafts 128, 130. For example, the first mechanism 136 can be configured such that rotating the first knob 144 (and/or an electric motor) relative to a housing of the handle 126 results in relative axial movement between the first and second shafts 128, 130.

The second and third mechanisms 138, 140 of the handle 126 are coupled and configured to manipulate the expansion components 134 (e.g., actuation shafts, support sleeves, etc.). For example, when the prosthetic valve 104 is coupled to the delivery apparatus 102 via the expansion components 134, the second mechanism 138 of the handle 126 can be used to radially expand and/or compress the prosthetic valve 104. While the third mechanism can be used to simultaneously couple and release the expansion components 134 to/from the prosthetic valve 104. Accordingly, the second mechanism 138 can be referred to as an "actuation mechanism" and/or an "expansion mechanism," and the third mechanism can be referred to as a "release mechanism" or a "coupling mechanism."

In the illustrated embodiment, the second and third mechanisms 138, 140 comprise a second and a third knob 146, 148 respectively, configured for actuating the second and third mechanisms 138, 140 to facilitate and/or restrict relative axial and/or rotational movement of the expansion components 134. In other embodiments, the second and third mechanisms 138, 140 can comprise of various other types of actuators, for example, electric motors, drive screws, gear assemblies, and/or other components.

The fourth mechanism 142 of the handle 126 is coupled to the nosecone shaft 132 and is configured to move the nosecone shaft 132 and the nosecone 106 axially relative to the first and second shafts 128, 130. As such, the fourth mechanism 142 can be referred to as a "nosecone mechanism."

In the illustrated embodiment, the fourth mechanism 142 comprises a slider 150 configured for actuating the fourth mechanism 142. Although not shown, the fourth mechanism 142 can comprise various other components configured to facilitate and/or restrict relative axial movement of the nosecone shaft 132 and the first and second shafts 128, 130. For example, in some embodiments, the fourth mechanism 142 can comprise one or more biasing members (e.g., springs) configured to bias the nosecone shaft 132 to a pre-determined axial position relative to the first and second shafts 128, 130. In other embodiments, the fourth mechanism can comprise a rotatable knob, an electric motor, and/or drive screw configured to convert relative rotational movement between the knob (and/or motor) and the housing into relative axial movement between the nosecone shaft and the first and second shafts.

During an implantation procedure, a delivery apparatus is advanced through a patient's vasculature. The patient's vasculature can include various curves, including some relative sharp curves (e.g., a native aortic arch as shown FIGS. 13-16). When advanced through a curve, the nosecone may be pushed axially against the inner wall of the vessel. This axial force in conjunction with the rigidity and length of conventional nosecones can result in undesirable gap formation between the outer shaft of the delivery device and the nosecone. For example, as a delivery apparatus is advanced around a native arch, the nosecone can contact the surrounding vessel wall and the nosecone may twist and/or rotate relative to the outer shaft. As the nosecone twists and rotates against the catheter it can apply a force against the inner wall of the outer shaft and causes the separation, which can lead to unwanted leakage into the delivery catheter and possible tissue damage.

Disclosed herein is a nosecone configured to reduce the axial forces and/or gap formation created as the delivery assembly is advanced around a curvature of a patient's vasculature lumen, such as the aortic arch. The disclosed nosecone can, for example, provide added bendability and freedom of movement to at the distal end of the delivery apparatus to help ease friction and limit gap formation during vasculature procedures. The nosecone can, in some instances, be coupled to a distal end of a delivery apparatus proximate to a delivery capsule. The nosecone disclosed herein can be used, for example, with the delivery apparatus 102.

Generally speaking, the disclosed nosecone operates by allowing a portion of the nosecone extending beyond the end of an outer shaft of a delivery apparatus to pivot relative to the portion of the nosecone located within the outer shaft. In this manner, the nosecone contacting the vasculature wall pivots relative to the remaining portions of the delivery apparatus, thereby reducing friction with respect to surrounding tissue and/or preventing separation between the nosecone and outer shaft.

Figure 7:
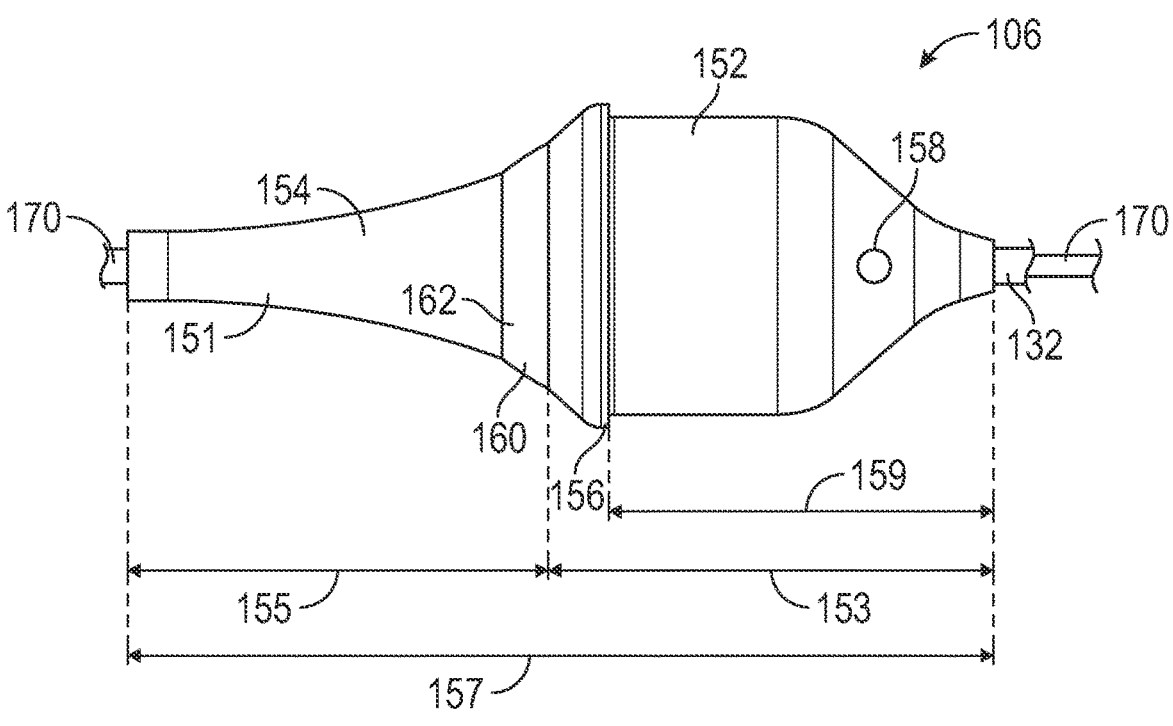
FIG. 7 is a side view of the nosecone coupled to a nosecone shaft of the delivery apparatus.
Figure 8:
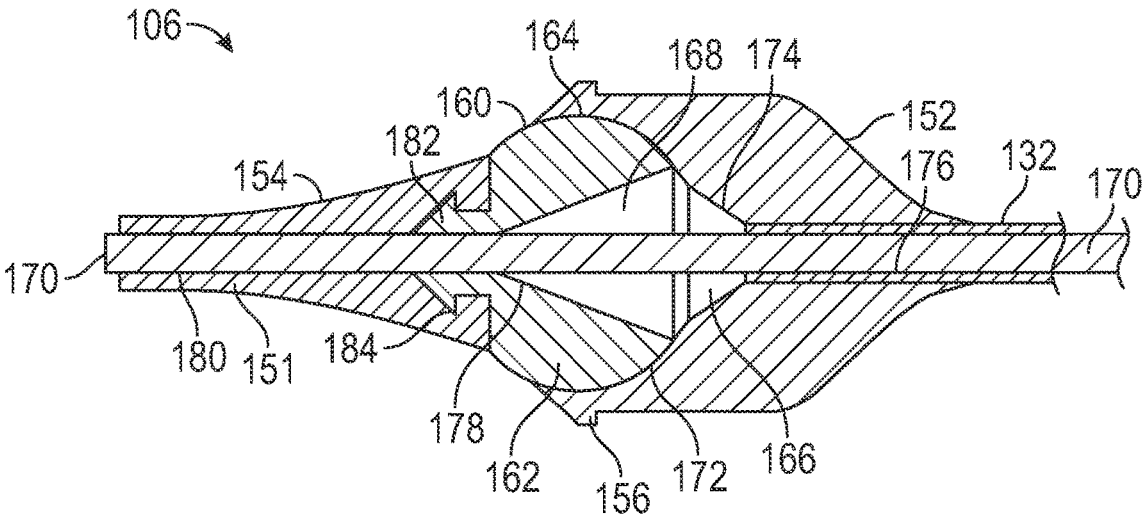
FIG. 8 is a cross-sectional side view of the nosecone coupled to the nosecone shaft of the delivery apparatus.

As shown in FIG. 1, the nosecone 106 can be coupled to the distal end portion of the delivery apparatus 102. FIGS. 7 and 8 (cross-sectional) show an exemplary nosecone 106 in a straight (or substantially straight) configuration. In the illustrated embodiment, the nosecone 106 can comprise a proximal end portion 152, a distal end portion 154, and an outer ridge 156 extending outwardly from and circumferentially around the surface of the proximal end portion 152. The nosecone 106 can have a total length 157 with the proximal end portion 152 having a length 153 and the distal end portion 154 having a length 155, wherein the length 155 is measured from the distal most point of the proximal end portion 152 to the distal most point of the distal end portion 154. The proximal end portion 152 can also have a shaft length 159 which is the length of the proximal end portion 152 disposed within the lumen of the first shaft 128 when the first shaft 128 extends over the proximal end portion 152 and buts against the outer ridge 156 (e.g., FIG. 6). The shaft length 159 is measured from the proximal most point of the outer ridge 156 to the proximal most point of the proximal end portion 152.

As shown in FIGS. 7 and 8, the proximal end portion 152 of the nosecone 106 can be coupled to the nosecone shaft 132 of the delivery apparatus 102 and have both an elongated shape and a tapered portion which narrows toward the nosecone shaft 132. The proximal end portion 152 can include a lumen 176 that receives the distal end portion of the nosecone shaft 132. The proximal end portion 152 can be coupled to the nosecone shaft 132 by a variety of methods, for example, such as overmolding, radio-frequency welding, through an adhesive, and/or a combination thereof. A combination of two or more of these methods, for example, can combine molding and/or welding with an adhesive added via an opening 158, which extends through the body of the proximal end portion 152 into the lumen 176 allowing the adhesive to bond to the nosecone shaft 132.

The distal end portion 154 is coupled to the proximal end portion 152 and can taper from an edge of the proximal end portion 152 to the distal end of the distal end portion 154. In the illustrated embodiment, the proximal end portion 152 and the distal end portion 154 of the nosecone 106 are pivotably and rotatably coupled. For example, the illustrated embodiment shows the proximal and distal end portions 152, 154 collectively comprising and being pivotably coupled by a ball and socket joint 160. The ball and socket joint 160 can include a ball 162 and a socket 164.

In some embodiments, the proximal end portion 152 comprises the socket 164 and the distal end portion 154 comprises the ball 162 of the joint 160 disposed within the socket 164. In this manner, the distal end portion 154 is configured to pivot and/or rotate relative to the proximal end portion 152 as the distal end portion contacts a surrounding vessel wall. As such, the distal end of the distal end portion 154 is configured to move in three-dimensional space relative to the proximal end portion 152. For example, the distal end portion 154 can move side-to-side and up and down relative to the proximal end portion 152.

In the illustrated embodiment, the socket 164 comprises a cavity in the proximal end portion that is sized and shaped to extend at least partially over and secure the ball 162 of the distal end portion 154 such that the distal end portion is free to pivot and rotate relative to the proximal end portion 152. In some embodiments, the motion of the distal end portion 154 can be limited to a pivoting motion (e.g., not rotatable) relative to the proximal end portion 152.

In other embodiments, the configuration of the ball and socket joint 160 can be reversed such that the proximal end portion 152 comprises the ball and the distal end portion 154 comprises the socket. Although not shown, the proximal end portion 152 and the distal end portion 154 can comprise and be pivotably coupled by other components which allow the distal end portion 154 to pivot and/or rotate relative to the proximal end portion 152. For example, the proximal and distal end portions 152, 154 can be coupled together by a rotatable hinge joint, knuckle joint, and/or other desired configurations.

Referring still to FIGS. 7 and 8, the proximal end portion 152 comprises a first lumen 166 and the distal end portion 154 comprises a second lumen 168, each lumen sized to permit a guidewire 170 to be passed therethrough. The first lumen 166 of the proximal end portion can comprise a socket lumen 172, a tapered lumen 174, and a shaft lumen 176 sized to receive the nosecone shaft 132 for coupling the proximal end portion 152 to the delivery apparatus 102. In the illustrated embodiment, the socket lumen 172 is proximate to the tapered lumen 174 and the tapered lumen 174 is proximate to the shaft lumen 176, each lumen configured to align (or substantially align) such that the first lumen 166 is continuous throughout the proximal end portion 152.

The second lumen 168 of the distal end portion 154 can comprise a tapered lumen 178 and a distal end lumen 180. In the illustrated embodiment, the tapered lumen 178 of the distal end portion 154 is located within the ball 162 and the distal end lumen 180 is located within a tapered section 151 of the distal end portion. As such, the distal end portion 154 of the nosecone 106 can comprise two portions coupled together to form a continuous lumen (e.g., the second lumen 168) to allow the guidewire 170 to extend therethrough. In the illustrated example, the ball 162 comprises a projection 182 and the tapered section 151 comprises a cavity 184 sized to form a snap-fit connection with the projection 182 such that the tapered section 151 and the ball 162 are securely coupled to each other. Alternatively, the ball 162 can comprise the cavity 184 and the tapered section 151 can comprise the projection 182. Although not shown, the tapered section 151 and the ball 162 can be releasably coupled and/or coupled by way of a threaded structure (e.g., bolt, screw, etc.), pin, adhesive, or other attachment means. In alternative embodiments, the distal end portion 154 can have a one-piece or unitary construction (e.g., the ball 162 and the tapered section 151 are portions of the same unitary body).

Figure 9:
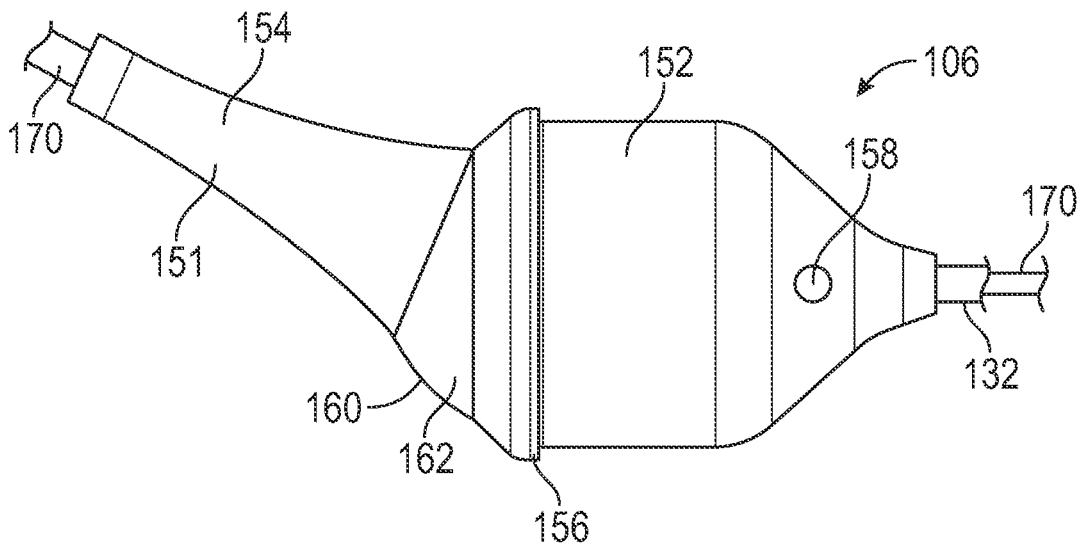
FIG. 9 is a side view of the nosecone coupled to the delivery apparatus showing a distal end portion of the nosecone pivoting relative to a proximal end portion of the nosecone.
Figure 10:
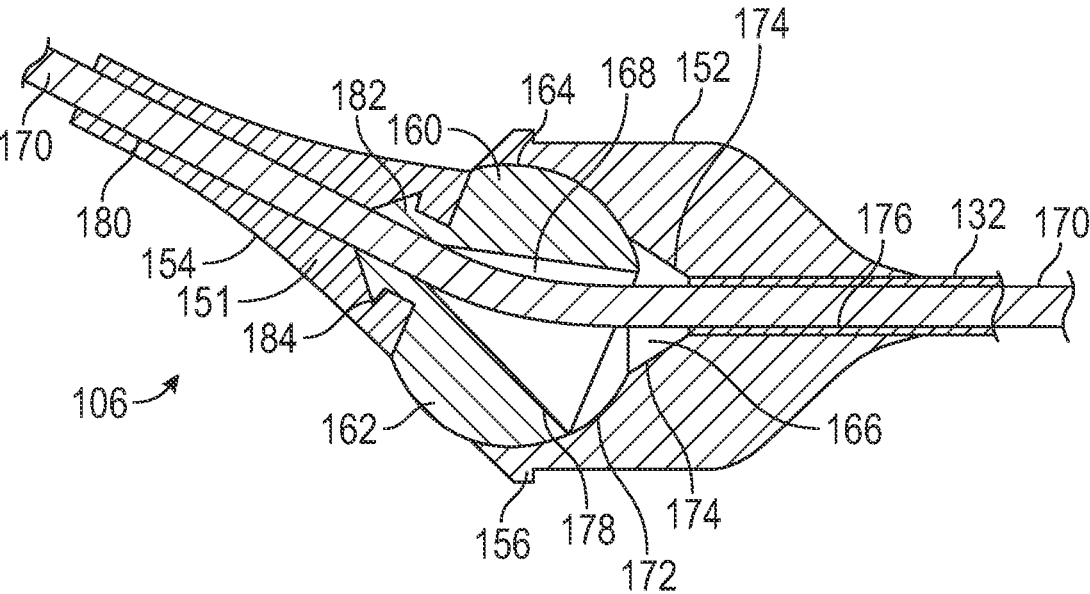
FIG. 10 is a cross-sectional side view of the nosecone coupled to the delivery apparatus showing the distal end portion of the nosecone pivoting relative to the proximal end portion of the nosecone.

As shown in FIGS. 9 and 10, the tapered lumens 174, 178 of the first and second lumens 166, 168 are configured to ensure a continuous lumen (e.g., pathway, channel, etc.) extends the length of the nosecone as the distal end portion 154 pivots and/or rotates relative to the proximal end portion 152. For example, in the illustrated embodiment of FIG. 10, the tapered lumens 174, 178 taper (i.e., narrow) in the opposite direction along the longitudinal axis of the nosecone 106. In this manner, as the distal end portion 154 (or alternatively the proximal end portions 152) pivots relative to the delivery apparatus 102, the wider diameter portion of the tapered lumens 174, 178 permit the guidewire 170 to extend through the nosecone 106 without obstruction and/or friction caused by contact from an otherwise smaller lumen diameter. As such, the nosecone 106 is configured to follow the curved path of the guidewire 170 as the delivery apparatus is advanced through and around the patient's vasculature native arch.

Figure 11:
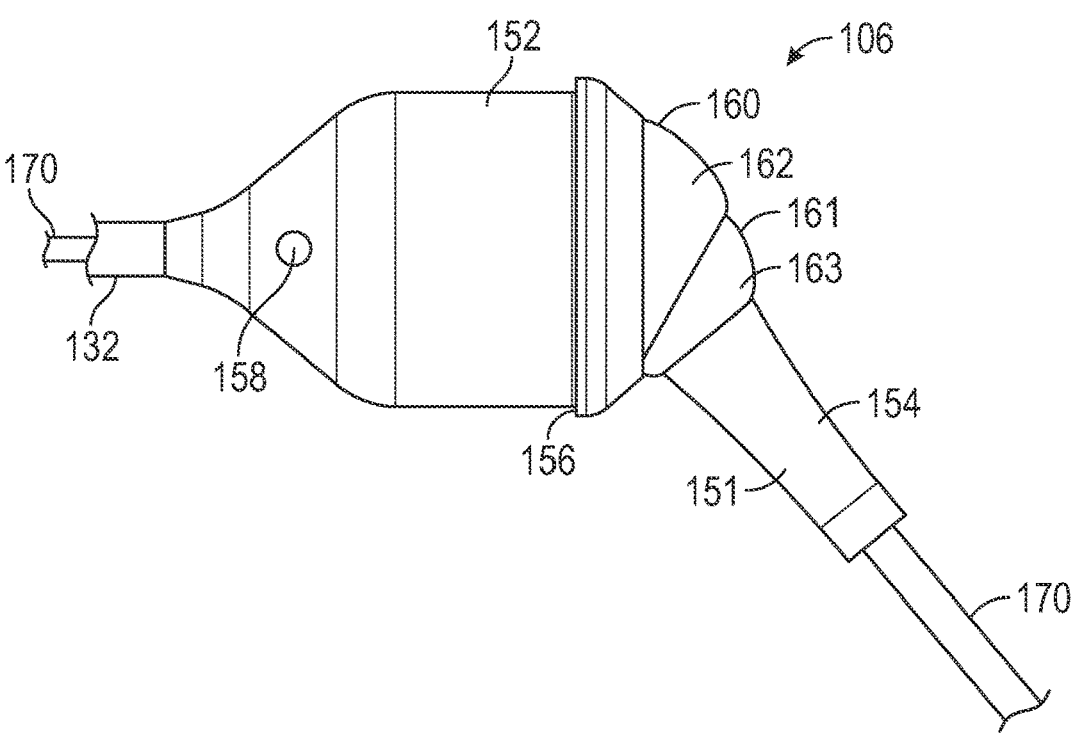
FIG. 11 is a side view of the nosecone coupled to the delivery apparatus showing a distal end portion of the nosecone pivoting relative to a proximal end portion and an intermediate portion.
Figure 12:
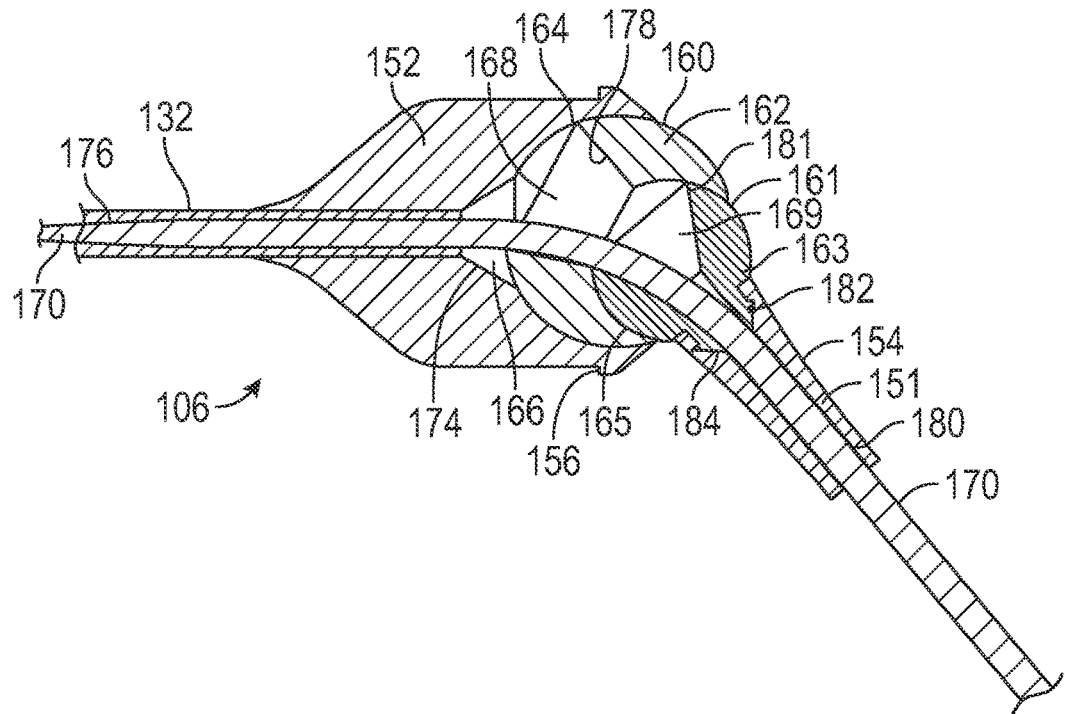
FIG. 12 is a cross-sectional side view of the nosecone of FIG. 11 coupled to the delivery apparatus showing the distal end portion of the nosecone pivoting relative to the proximal end portion and the intermediate portion.

Referring to FIGS. 11 and 12, the nosecone 106 can have one or more additional ball and socket joints in addition to the ball and socket joint 160. For example, the ball 162 of the first joint 160 can act as an intermediate portion defining a second socket 165 that is sized and shaped to extend partially over and secure the second ball 163 of the distal end portion 154. As such, the distal end portion 154 is pivotably and rotatably coupled to the ball 162 of the joint 160. In this manner, the distal end portion 154 is configured to pivot and/or rotate relative to the ball 162 and the proximal end portion 152 as the distal end portion 154 contacts a surrounding vessel wall. In the illustrated embodiments, the ball 163 is securely coupled to the tapered section 151 by a snap-fit connection comprising the projection 182 extending into the cavity 184 of the tapered section 151. Alternatively, the ball 163 can comprise the cavity 184 and the tapered section 151 can comprise the projection 182.

The distal end portion 154 can also comprise a third lumen 169 sized to permit the guidewire 170 through its length while the ball 162 can comprise the second lumen 168. As shown in FIG. 12, the third lumen 169 can comprise a tapered lumen 181 and the distal end lumen 180 extending through the projection 182 and tapered section 151 and the second lumen 168 can comprise the tapered lumen 178 and the socket lumen 179 extending through the ball 162. As such, the tapered lumens 174, 178, 181 of the first, second, and third lumens 166, 168, 169 are configured to ensure a continuous lumen extends through the length of the nosecone as the distal end portion 154 pivots and/or rotates relative to the proximal end portion 152 and the ball 162. In some embodiments, the configuration of the ball and socket joint 161 can be reversed such that the intermediate portion (e.g., ball 162) can comprise the second ball 163 extending outwardly in a distal direction and disposed within the socket 165 defined by the distal end portion 154 and facing in a proximal direction. In alternative embodiments, the nosecone 106 can comprise more than two ball and socket joints connected end-to-end.

Referring back to FIGS. 1 and 4, a proximal end portion of the first shaft 128 can be coupled to and extend distally from the handle 126. The first shaft 128 comprises a lumen for housing the second shaft 130 of the delivery apparatus 102. The distal end portion of the first shaft 128 is configured to receive the prosthetic valve 104 in the radially compressed configuration (e.g., FIGS. 5 and 6). As such, the first shaft 128 can be referred to as a "sheath" or a "delivery capsule" 186. Alternatively, the delivery capsule 186 can be a separately formed component coupled to the distal end portion of the first shaft 128. As shown in FIG. 5, the second shaft 130 extends coaxially through and is axially movable relative to the first shaft 128 and can comprise a single (or multiple) lumen extending coaxially therethrough which houses a portion of the expansion components 134.

The prosthetic valve 104 can be releasably coupled to a distal end portion of the delivery apparatus 102 to form the delivery assembly (e.g., FIGS. 1 and 5-6), and the delivery apparatus 102 can be used to implant the prosthetic valve 104 within a patient's body (e.g., FIGS. 13-16). With the prosthetic valve 104 releasably coupled to the delivery apparatus 102, the prosthetic heart valve 104 can be radially compressed using a crimping device, or other means, for example, actuators or recompression members (e.g., the expansion and/or compression components 134) and inserted into the delivery capsule 186.

FIGS. 5 and 6 show the prosthetic valve 104 in a radially compressed configuration. The first shaft 128 of the delivery apparatus 102 can be advanced over the second shaft 130 of the delivery apparatus 102, the prosthetic valve 104, and the proximal end portion 152 of the nosecone 106. As such, the prosthetic valve 104 and the proximal end portion 152 of the nosecone 106 are disposed within the lumen of the first shaft 128 (e.g., within the delivery capsule 186). As shown in FIG. 6, the capsule 186 extends over the tapered portion of the proximal end portion 152 and abuts the ridge 156 of nosecone 106, creating a flush (or substantially flush) surface between the capsule 186 and the nosecone 106. The advancement of the first shaft 128 can be accomplished, for example, by actuating the first mechanism 136 of the handle 126.

The distal end portion of the delivery assembly 100 can then be inserted into a patient's vasculature, and the prosthetic valve 104 can be advanced to an implantation location using the delivery apparatus 102. For example, FIGS. 13-16 show an exemplary implantation procedure for implanting the prosthetic valve 104 within a patient's heart 188 using a transfemoral delivery procedure. In other embodiments, various other delivery procedures can be used, such as transventricular, transapical, transseptal, etc.

Figure 13:
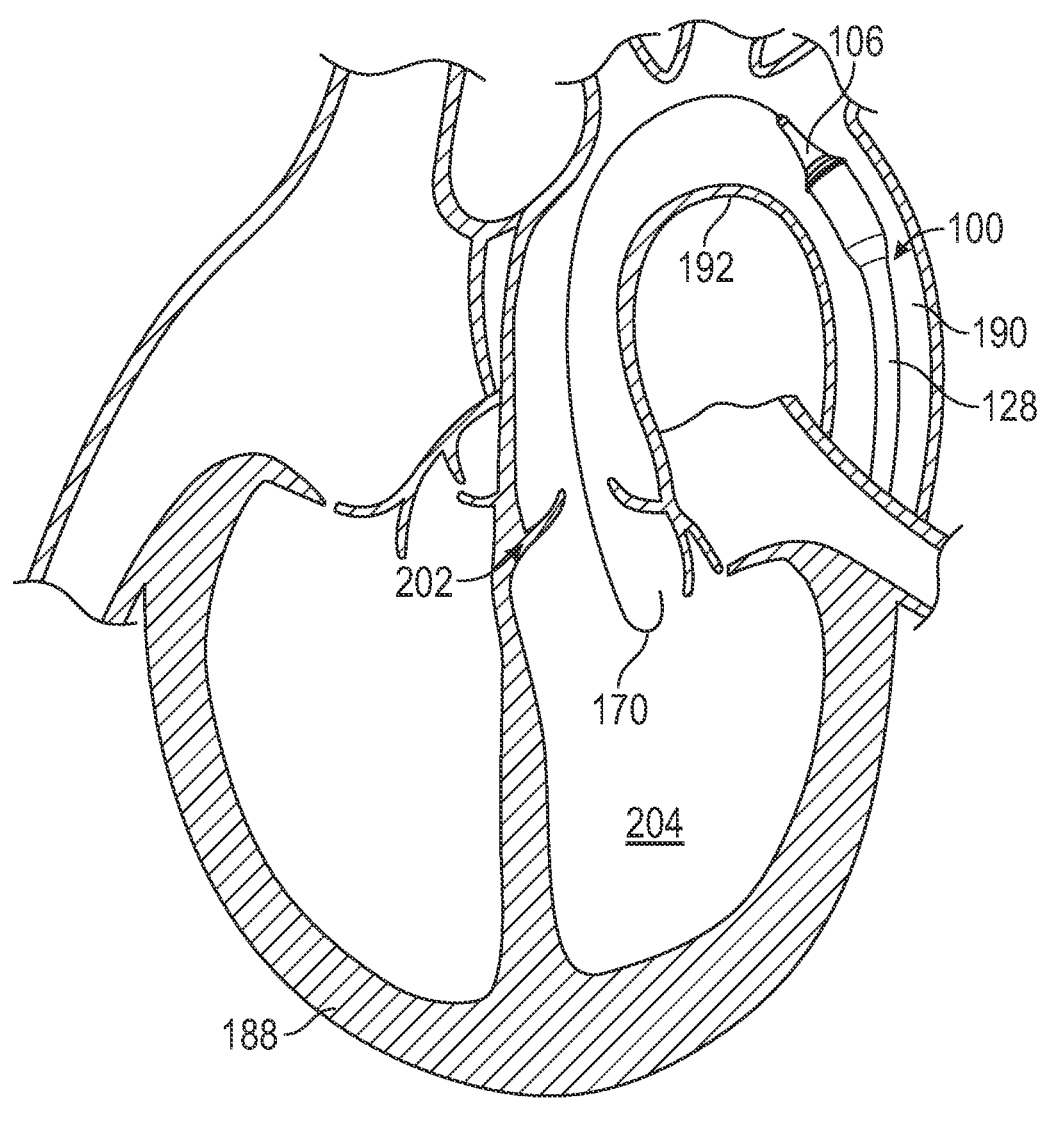
FIG. 13 depicts the distal end of the delivery assembly comprising the nosecone advancing through a vasculature arch of a heart (shown in cross-section).
Figure 14:
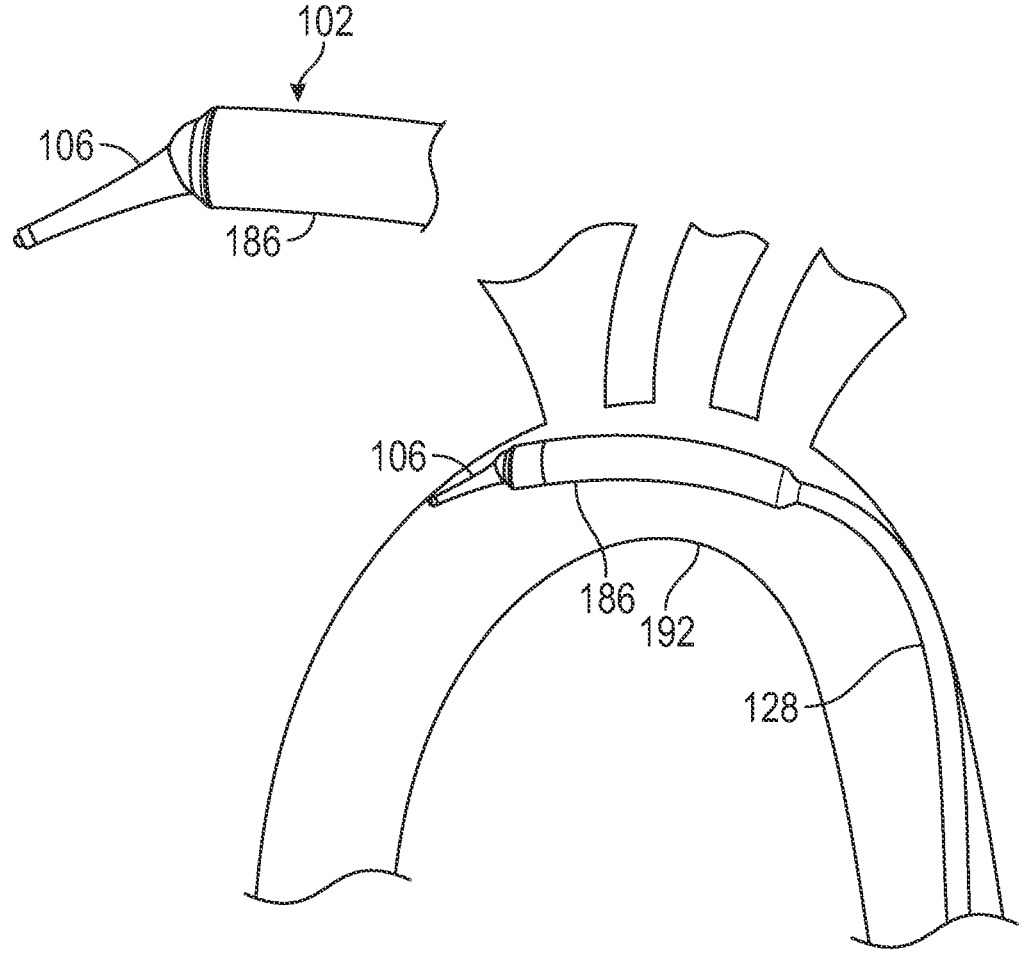
FIG. 14 depicts a rigid section of the delivery assembly contacting a vasculature wall of the heart showing the distal end of the nosecone pivoting relative to the delivery assembly.

Referring to FIG. 13, the distal end portion of the delivery assembly 100 is inserted into the vasculature of a patient's heart 188 such that the first shaft 128 and nosecone 106 extend through the patient's aorta 190 and approach the aortic arch 192. As shown in FIG. 14, as an axial force is applied to the delivery apparatus 102 (e.g., at the handle 126) to advance the delivery apparatus 102 around the aortic arch 192, the nosecone 106, first shaft 128, and delivery capsule 186 may contact the surrounding aortic wall. Collectively, the nosecone 106, the delivery capsule 186 and a portion of the first shaft 128 proximal to the capsule 186 can form a rigid section.

Generally, the rigid section of conventional delivery systems lacks any significant flexibility and therefore, navigating the aortic arch 192 forces a standard, rigid nosecone to twist and/or rotate relative to the first shaft as it contacts the aortic wall. As a result, a standard nosecone applies an outward force against the inner wall of the capsule as it twists and/or rotates during the contact, creating separation between the capsule and nosecone. Additionally, the rigidity of a standard nosecone within the rigid section typically requires a greater axial force to circumvent the aortic arch 192, thereby causing high frictional forces against the aortic wall, potentially damaging native tissue. However, the nosecone 106 disclosed herein, adds bendability to and reduces the overall length of the rigid section, limiting separation between the nosecone and shaft, as well as the friction generally created to navigate the delivery apparatus around the aortic arch 192.

Referring to FIG. 14, the rigid section of the illustrated embodiment comprises the length 153 of the proximal end portion 152 (see FIG. 7), the delivery capsule 186, and a rigid section of the first shaft 128, which is a region of the first shaft 128 having low bendability and/or flexibility relative to the delivery capsule 186. By making the distal end portion 154 of the nosecone 106 pivotable (and rotatable) relative to the proximal end portion 152, the overall length of the rigid section is significantly reduced in comparison to conventional systems. First, for example, as shown in FIG. 14, the portion of the rigid section typically attributable to a conventional nosecone (i.e., the total length of a conventional nosecone) is reduced nearly by the entire length 155 of the distal end portion 154 (e.g., shown in FIG. 7) because the distal end portion 154 is no longer rigid (i.e., stationary) relative to the proximal end portion 152 and delivery apparatus 102.

Second, the portion of the nosecone 106 that resides within the capsule 186 during delivery can be shorter than that of a corresponding portion of a standard nosecone in a conventional system. For example, conventional nosecones typically require a longer proximal portion that extends into the capsule in order to reduce the separation between the nosecone and the capsule. In other words, because of the force a standard nosecone applies to the inner wall of the capsule during delivery, the proximal portion of the nosecone must extend farther into the capsule to reduce gap formation. Therefore, a further reduction of the overall length of the rigid section is achieved by having the distal end portion 154 of the nosecone 106 being pivotable and/or rotatable relative to the rest of delivery apparatus 102 because the shaft length 159 of the proximal end portion 152 extending into the delivery capsule 186 can have a length shorter than generally necessary to prevent gap formation.

Consequently, preventing gap formation between the nosecone 106 and the capsule 186 allows the capsule 186 to remain in constant contact (or substantially in constant) with the outer ridge 156 of the nosecone 106 as the delivery apparatus is advanced around the aortic arch 192. In this manner, the nosecone 106 disclosed herein substantially prevents leakage into the delivery catheter (e.g., the first shaft 128). Additionally, as the above indicates, the nosecone 106 disclosed herein reduces the overall length of the rigid section regardless of any reduction in the length of a prosthetic valve, delivery capsule, and/or rigid first shaft.

Figure 15:
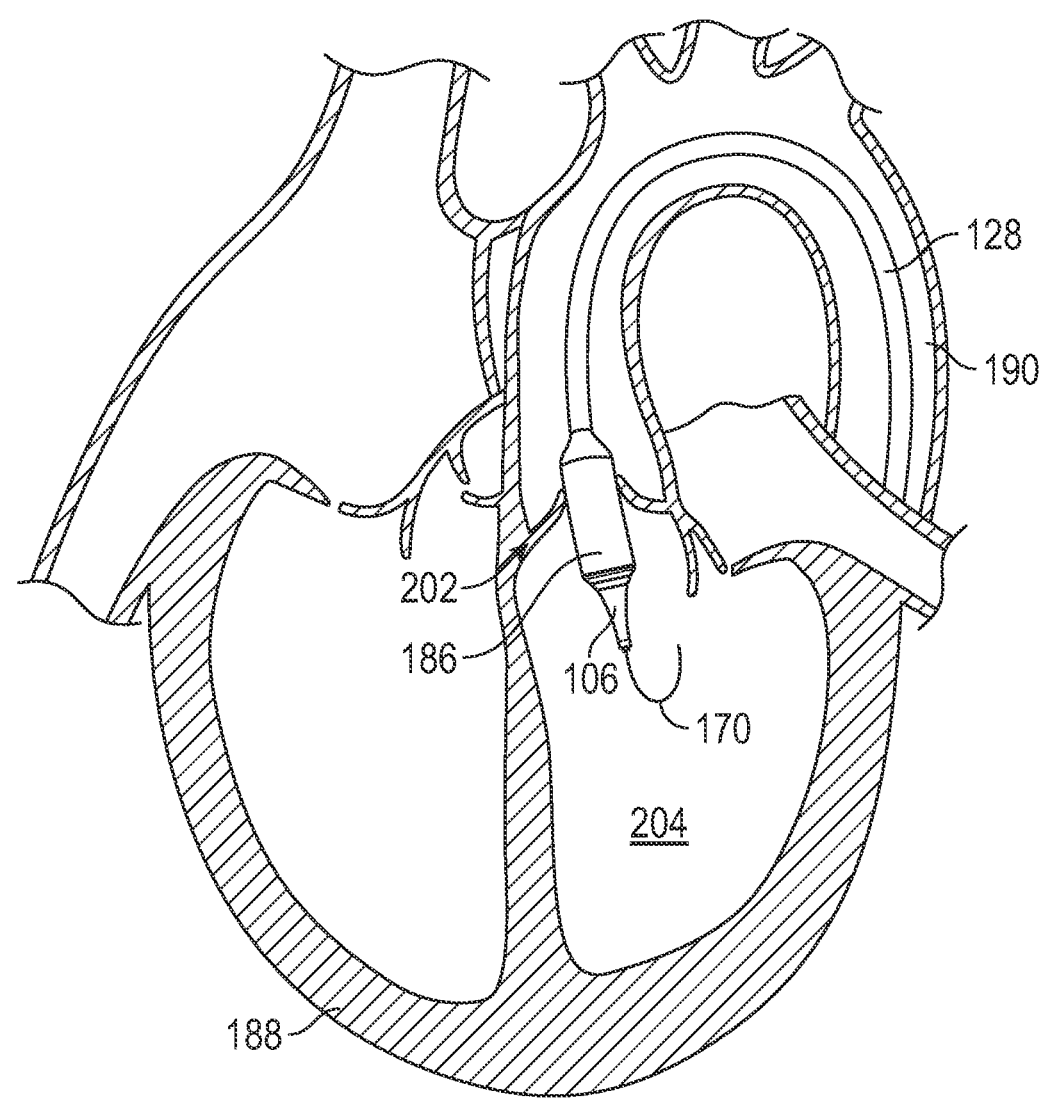
FIGS. 15 and 16 depict an exemplary implantation procedure in which the prosthetic heart valve is implanted in a heart (show in cross-section) with the delivery apparatus.
Figure 16:
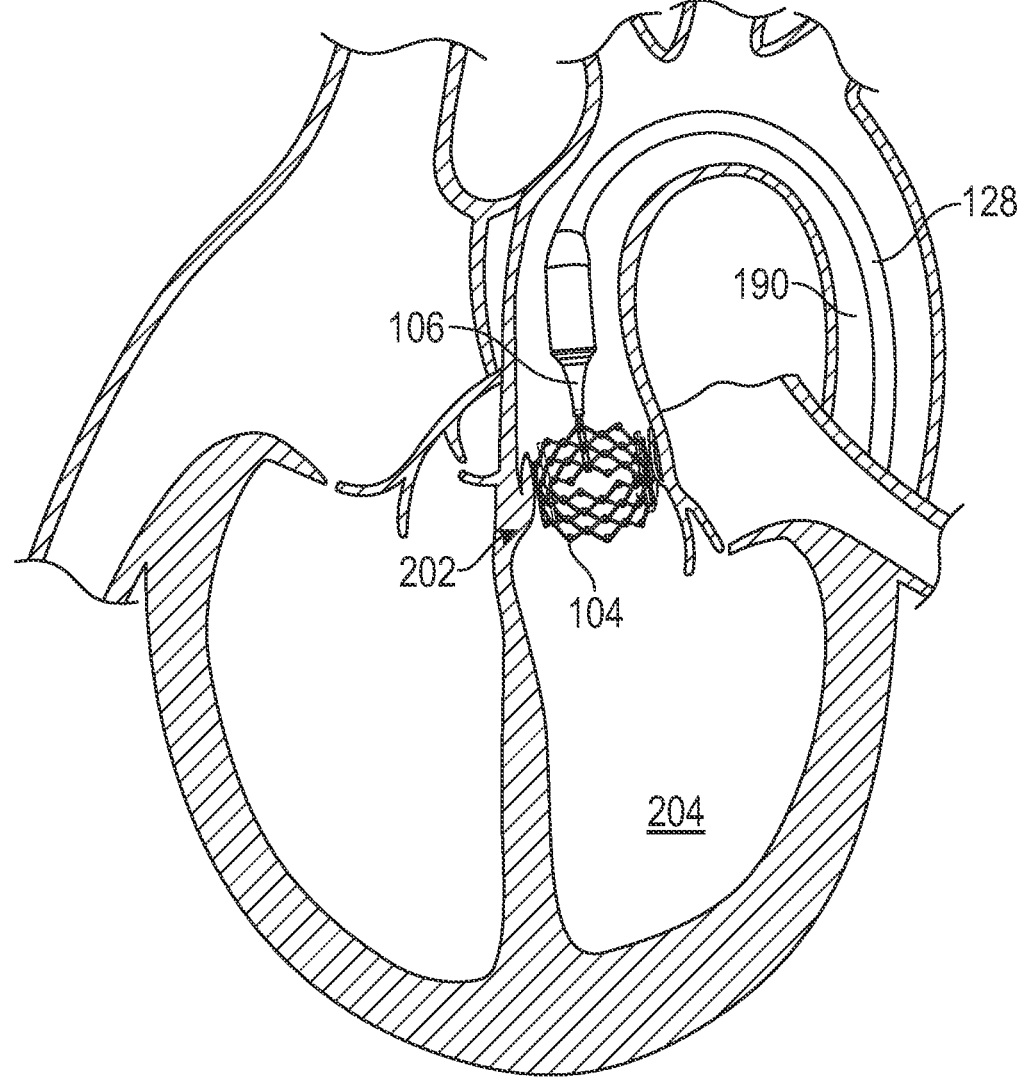

Turning to FIGS. 15-16, the distal end portion of the delivery assembly 100 is inserted into a patient's vasculature until the capsule 186 and nosecone 106 extend through the patient's native aortic annulus 202 and into the left ventricle 204 of the patient's heart 188. The prosthetic valve 104 can then be deployed from the first shaft 128 of the delivery apparatus 102 by actuating the first mechanism 136 of the handle 126, which moves the capsule 186 of the delivery apparatus 102 proximally relative to the second shaft 130 of the delivery apparatus 102 (and/or moves the second shaft 130 distally relative to the first shaft 128). Prior to or after retracting the capsule 186, the nosecone 106 can be advanced distally relative to the capsule and the prosthetic valve. As discussed above, the nosecone 106 can be advanced distally by activation of the fourth mechanism 142 (FIG. 4). The prosthetic valve 104 can then be radially expanded, such as by activation of the expansion components 134 via the second mechanism 138, as previously described.

As shown in FIG. 16, after the prosthetic valve 104 is radially expanded, the prosthetic valve 104 can then be released from the delivery apparatus 102. Thereafter, the nosecone 106 can be retracted back into the capsule 186 and/or the capsule 186 can be advanced distally back over the nosecone 106 until the end of the capsule 186 engages the ridge 156 of the nosecone, as depicted in FIG. 16. The delivery apparatus 102 can then be removed from the patient's body.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1: A delivery apparatus for an implantable medical device comprising: a handle; a shaft having a proximal end portion and a distal end portion, the proximal end portion being coupled to the handle; and a nosecone coupled to the distal end portion of the shaft, wherein the nosecone comprises a proximal end portion and a distal end portion pivotably coupled to the proximal end portion.

Example 2: The delivery apparatus of any example herein, particularly example 1, wherein the nosecone comprises a ball and socket joint coupling the proximal end portion of the nosecone to the distal end portion of the nosecone.

Example 3: The delivery apparatus of any example herein, particularly example 2, wherein the ball and socket joint comprises a ball disposed in a socket, wherein one of the proximal end portion and the distal end portion comprises the ball and the other of the proximal end portion and distal end portion comprises the socket.

Example 4: The delivery apparatus of any example herein, particularly example 3, wherein the proximal end portion comprises the socket and the distal end portion comprises the ball.

Example 5: The delivery apparatus of any example herein, particularly example 3, wherein the distal end portion comprises the socket and the proximal end portion comprises the ball.

Example 6: The delivery apparatus of any example herein, particularly example 4, wherein the distal end portion comprises a tapered end portion, wherein the tapered end portion is coupled to the ball.

Example 7: The delivery apparatus of any example herein, particularly example 5, wherein the proximal end portion comprises a tapered end portion, wherein the tapered end portion is coupled to the ball.

Example 8: The delivery apparatus of any example herein, particularly any one of examples 6-7, wherein the tapered end portion has a cavity and the ball has a projection, wherein the cavity is configured to receive the projection such that the tapered end portion is connected to the ball.

Example 9: The delivery apparatus of any example herein, particularly any one of examples 6-7, wherein the ball has a cavity and the tapered end portion has a projection, wherein the cavity is configured to receive the projection such that the ball is connected to the tapered end portion.

Example 10: The delivery apparatus of any example herein, particularly example any one of examples 1-9, wherein the proximal end portion comprises a first lumen and the distal end portion comprises a second lumen, wherein the first lumen and the second lumen are sized to receive a guidewire therethrough.

Example 11: The delivery apparatus of any example herein, particularly example 10, wherein the distal end portion of the shaft extends into the first lumen of the proximal end portion of the nosecone.

Example 12: The delivery apparatus of any example herein, particularly example 11, wherein the proximal end portion of the nosecone is molded or welded to the distal end portion of the shaft.

Example 13: The delivery apparatus of any example herein, particularly any one of examples 10-12, wherein the first lumen of the proximal end portion and the second lumen of the distal end portion each have a tapered segment, wherein the tapered segments of the proximal end portion and the distal end portion are proximate to one another.

Example 14: The delivery apparatus of any example herein, particularly any one of examples 1-13, wherein the proximal end portion of the nosecone has a ridge extending radially outwardly from an outer surface of the proximal end portion.

Example 15: The delivery apparatus of any example herein, particularly example 14, wherein the ridge extends circumferentially around the outer surface of the proximal end portion.

Example 16: The delivery apparatus of any example herein, particularly any one of examples 14-15, wherein the shaft comprises a first shaft and the delivery apparatus comprises a second shaft extending over the first shaft, the second shaft comprising a delivery capsule along a distal end section thereof, the delivery capsule configured to retain a medical implant in a radially collapsed state for delivery into a patient, wherein a distal end section of the delivery capsule is sized to extend over the proximal end portion of the nosecone.

Example 17; The delivery apparatus of any example herein, particularly any one of examples 14-16, wherein the distal end section of the delivery capsule abuts the ridge while extending over the proximal end portion of the nosecone.

Example 18: The delivery apparatus of any example herein, particularly any one of examples 1-17, wherein the proximal end portion and the distal end portion of the nosecone are rotatably coupled to each other.

Example 19: A delivery apparatus for an implantable medical device comprising: a handle; a first shaft and a second shaft extending over the first shaft, wherein the first shaft comprises a proximal end portion and a distal end portion, the proximal end portion being coupled to the handle, and the second shaft comprises a delivery capsule along a distal end thereof; and a nosecone coupled to the distal end portion of the first shaft, the nosecone comprising a proximal end portion and a distal end portion pivotably coupled to the proximal end portion by a ball and socket joint, wherein the ball and socket joint comprises a ball disposed in a socket, wherein one of the proximal end portion and the distal end portion comprises the ball and the other of the proximal end portion and distal end portion comprises the socket; wherein the proximal end portion of the nosecone comprises a first lumen and the distal end portion of the nosecone comprises a second lumen, wherein the first lumen and the second lumen are sized to receive a guidewire therethrough, and the distal end portion of the first shaft extends into the first lumen of the proximal end portion; wherein the delivery capsule is configured to retain a medical implant in a radially collapsed state for delivery into a patient, wherein a distal end section of the delivery capsule is sized to extend over the proximal end portion of the nosecone.

Example 20: A delivery apparatus for an implantable medical device comprising: a handle; a shaft having a proximal end portion and a distal end portion, the proximal end portion being coupled to the handle; and a nosecone coupled to the distal end portion of the shaft, wherein the nosecone comprises a proximal end portion and a distal end portion pivotably coupled to the proximal end portion by a ball and socket joint, the ball and socket joint comprising a ball disposed in a socket, wherein the proximal end portion comprises the socket and the distal end portion comprises the ball.

Example 21: The delivery apparatus of any example herein, particularly example 20, wherein the proximal end portion of the nosecone comprises a first lumen and the distal end portion of the nosecone comprises a second lumen, wherein the first and second lumens are sized to receive a guidewire therethrough.

Example 22: The delivery apparatus of any example herein, particularly example 21, wherein the distal end portion of the shaft extends into the first lumen and the proximal end portion of the nosecone, wherein the proximal end portion is adhered, welded, molded, or a combination thereof, to the distal end portion of the shaft.

Example 23: The delivery apparatus of any example herein, particularly any one of examples 21-22, wherein the first lumen comprises a first tapered lumen and the second lumen comprises a second tapered lumen, wherein the first tapered lumen and the second tapered lumen are proximate to and taper in opposite directions from one another.

Example 24: The delivery apparatus of any example herein, particularly example 23, wherein the first tapered lumen and the second tapered lumen are configured to permit the first lumen and the second lumen to be in constant communication as the proximal end portion and the distal end portion pivot relative to each other.

Example 25: The delivery apparatus of any example herein, particularly any one of examples 23-24, wherein the first lumen comprises a socket lumen, the first tapered lumen, and a shaft lumen, wherein the socket lumen is proximate to the first tapered lumen and the first tapered lumen is proximate to the shaft lumen.

Example 26: The delivery apparatus of any example herein, particularly example 25, wherein the socket lumen, the first tapered lumen, and the shaft lumen each comprise an inner diameter, wherein the inner diameter of the socket lumen is greater than or equal to the inner diameter of the first tapered lumen, and the inner diameter of the first tapered lumen is greater than or equal to the inner diameter of the shaft lumen.

Example 27: The delivery apparatus of any example herein, particularly any one of examples 23-25, wherein the second lumen comprises the second tapered lumen and a distal end lumen.

Example 28: The delivery apparatus of any example herein, particularly example 27, wherein the distal end portion comprises a tapered portion and the ball, wherein the tapered portion comprises the distal end lumen and the ball comprises the second tapered lumen.

Example 29: The delivery apparatus of any example herein, particularly any one of examples 25-28, wherein the proximal end portion comprises an outer surface and a ridge extending radially outwardly and circumferentially around the outer surface.

Example 30: The delivery apparatus of any example herein, particularly example 29, wherein the ridge is proximate and concentric to the socket lumen.

Example 31: A delivery apparatus for an implantable medical device comprising: a handle; a shaft having a proximal end portion and a distal end portion, the proximal end portion being coupled to the handle; and a nosecone coupled to the distal end portion of the shaft, the nosecone comprising a proximal end portion, a distal end portion coupled to the proximal end portion, and a coupling means for coupling the distal end portion and the proximal end portion, the coupling means permitting pivoting movement of the distal end portion relative to the proximal end portion.

Example 32: The delivery apparatus of any example herein, particularly example 31, wherein the distal end portion comprises a first lumen and the distal end portion comprises a second lumen, wherein the first lumen and the second lumen are configured to receive a guidewire therethrough.

Example 33: The delivery apparatus of any example herein, particularly example 32, wherein the coupling means coupling the distal end portion and the proximal end portion permits rotating movement of the distal end portion relative to the proximal end portion such that the distal end portion is rotatable relative to the guidewire.

Example 34: The delivery apparatus of any example herein, particularly any one of examples 31-33, wherein the coupling means comprises a ball disposed in a socket, wherein the distal end portion comprises the ball and the proximal end portion comprises the socket.

Example 35: The delivery apparatus of any example herein, particularly any one of examples 31-34, wherein the coupling means comprises a ball disposed in a socket, wherein the distal end portion comprises the ball and the proximal end portion comprises the socket.

Example 36: The delivery apparatus of any example herein, particularly example 32, wherein the first lumen and the second lumen each include a tapered section, wherein the tapered section of the first lumen and the tapered section of the second lumen permit constant communication between the first lumen and the second lumen.

Example 37: The delivery apparatus of any example herein, particularly any one of examples 31-36, wherein the distal end portion comprises a first section and a second section, the first section having a projection and the second section having a cavity, wherein the cavity is configured to receive the projection such that the first section is coupled to the second section.

Example 38: The delivery apparatus of any example herein, particularly any one of examples 31-37, wherein the proximal end portion comprises a circumference, an outer surface, and a ridge extending outwardly from the outer surface and circumferentially around the circumference of the proximal end portion.

Example 39: The delivery apparatus of any example herein, particularly any one of examples 32-38, wherein the shaft comprises a first shaft and the delivery apparatus comprises a second shaft extending over the first shaft, the second shaft comprising a delivery capsule along a distal end section thereof, the delivery capsule configured to retain a medical implant in a radially collapsed state for delivery into a patient, wherein a distal end section of the delivery capsule is sized to extend over the proximal end portion of the nosecone.

Example 40: The delivery apparatus of any example herein, particularly example 38, wherein the ridge and the first lumen are concentric about a central longitudinal axis of the proximal end portion.

Example 41: The delivery apparatus of any example herein, particularly any one of examples 31-41, wherein the distal end portion has a length greater than a length of the proximal end portion.

Example 42: An implantable medical device delivery assembly comprising: a delivery apparatus comprising a handle, a nosecone, and a shaft having a proximal end portion and a distal end portion, w % herein the proximal end portion is coupled to the handle and the distal end portion is coupled to the nosecone; and an expandable implantable medical device mounted in a radial configuration around the distal end portion of the shaft; wherein the nosecone comprises a proximal end portion and a distal end portion pivotably coupled to the proximal end portion.

Example 43: An implantable medical device delivery assembly comprising: a delivery apparatus comprising a handle, a nosecone, and a shaft having a proximal end portion and a distal end portion, w % herein the nosecone is coupled to the distal end portion and the proximal end portion is coupled to the handle; and an expandable implantable medical device mounted in a radial configuration around the distal end portion of the shaft; wherein the nosecone comprises a proximal end portion and a distal end portion pivotably coupled to the proximal end portion by a ball and socket joint, wherein one of the proximal end portion and the distal end portion comprises the ball and the other of the proximal end portion and distal end portion comprises the socket.

Example 44: An implantable medical device delivery assembly comprising: a delivery apparatus comprising a handle, a nosecone, a first shaft, and a second shaft extending over the first shaft, the first shaft comprising a distal end portion and a proximal end portion coupled to the handle, the second shaft comprising a delivery capsule along a distal end section thereof, and the nosecone comprising a proximal end portion and a distal end portion pivotably coupled to the proximal end portion; and an expandable implantable medical device mounted in a radially compressed configuration around the distal end portion of the first shaft and within the delivery capsule of the second shaft; and wherein the distal end portion and the proximal end portion of the nosecone are pivotably coupled by a ball and socket joint comprising a ball disposed in a socket, wherein the distal end portion comprises the ball and the proximal end portion comprises the socket, wherein a distal end section of the delivery capsule is sized to extend over the proximal end portion of the nosecone.

Example 45: The delivery assembly of any example herein, particularly example 44, wherein the proximal end portion of the nosecone comprises an outer surface and an outer ridge, wherein the outer ridge extends outwardly from the outer surface and circumferentially around the proximal end portion, wherein the distal end section of the delivery capsule abuts the outer ridge while extending over the proximal end portion of the nosecone.

Example 46: The delivery assembly of any example herein, particularly example 45, wherein the outer ridge comprises a first outer circumference and the distal end section of the delivery capsule comprises a second outer circumference, wherein the first outer circumference is equal to or substantially equal to the second outer circumference such that the outer ridge and the distal end section of the delivery capsule form a continuous outer surface extending from the nosecone to the handle.

Example 47: A method for delivering an implantable medical device, the method comprising: advancing an expandable implantable medical device mounted in a radially compressed configuration around a distal end portion of a shaft of a delivery apparatus into a native lumen of a patient such that at least a distal end portion of a nosecone of the delivery apparatus contacts a vasculature wall of the patient, wherein contact between the nosecone and the vasculature wall causes the distal end portion of the nosecone to pivot relative to a proximal end portion of the nosecone.

Example 48: The method of any example herein, particularly example 47, wherein contact between the nosecone and the vasculature wall causes the distal end portion of the nosecone to rotate relative to the proximal end portion of the nosecone.

Example 49: A method for implanting a prosthetic valve into an aortic annulus of a patient, the method comprising: advancing an expandable prosthetic valve and a distal end portion of a shaft of a delivery apparatus into an aorta of the patient, wherein the prosthetic valve is mounted in a radially compressed configuration around the distal end portion of the shaft, such that at least a distal end portion of a nosecone of the delivery apparatus contacts a wall of the aorta, wherein of the distal end portion of the nosecone is pivotably coupled to a proximal end portion of the nosecone, wherein the proximal end portion is coupled to the distal end portion of the shaft; wherein contact between the nosecone and the wall of the aorta causes the distal end portion of the nosecone to pivot relative to the proximal end portion of the nosecone, the distal end portion of the shaft, and the prosthetic valve; inserting the distal end portion of the shaft into an aortic annulus of the patient such that the nosecone extends through the aortic annulus and into a left ventricle of the patient; and expanding the prosthetic valve from a radially compressed state to a radially expanded state within the aortic annulus.

Example 50: A delivery apparatus for an implantable medical device comprising: a handle; a first shaft and a second shaft extending over the first shaft, wherein the first shaft comprises a proximal end portion and a distal end portion, the proximal end portion being coupled to the handle, and the second shaft comprises a delivery capsule along a distal end thereof; and a nosecone coupled to the distal end portion of the first shaft, the nosecone comprising a proximal end portion, an intermediate portion pivotably coupled to the proximal end portion by a first ball and socket joint, and a distal end portion pivotably coupled to the intermediate portion by a second ball and socket joint, wherein each ball and socket joint comprises a ball disposed in a socket.

Example 51: The delivery apparatus of any example herein, particularly example 50, wherein one of the proximal end portion and the intermediate portion comprises the first ball and the other of the proximal end portion and intermediate portion comprises the first socket.

Example 52: The delivery apparatus of any example herein, particularly any one of examples 50-51, wherein one of the intermediate portion and the distal end portion comprises the second ball and the other of the intermediate portion and the distal end portion comprises the second socket.

Example 53: The delivery apparatus of any example herein, particularly example 50, wherein the intermediate portion comprises the ball and the proximal end portion comprises the socket of the first ball and socket joint.

Example 54: The delivery apparatus of any example herein, particularly any one of examples 50 or 53, wherein the distal end portion comprises the ball and the intermediate portion comprises the socket of the second ball and socket joint.

Example 55: The delivery apparatus of any example herein, particularly any one of examples 50-54, wherein the proximal end portion comprises a first lumen, the intermediate portion comprises a second lumen, and the distal end portion comprises a third lumen, wherein the first, second, and third lumens are sized to receive a guidewire therethrough.

Example 56: A delivery apparatus for an implantable medical device comprising: a handle; a shaft having a proximal end portion and a distal end portion, the proximal end portion being coupled to the handle; and a nosecone coupled to the distal end portion of the shaft, wherein the nosecone comprises a proximal end portion and a distal end portion pivotably coupled to the proximal end portion by a plurality of ball and socket joints.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as my invention all that comes within the scope and spirit of these claims.

The invention claimed is:

1. A delivery apparatus for an implantable medical device comprising:

a handle;

a shaft having a shaft proximal end portion and a shaft distal end portion, the shaft proximal end portion being coupled to the handle; and a nosecone coupled to the shaft distal end portion, wherein the nosecone comprises a nosecone proximal end portion and a nosecone distal end portion pivotably coupled to the nosecone proximal end portion, wherein the nosecone proximal end portion is distally disposed relative to a portion of the shaft configured to receive the implantable medical device therearound.

2. The delivery apparatus of claim 1, wherein the nosecone comprises a ball and socket joint coupling the nosecone proximal end portion to the nosecone distal end portion.

3. The delivery apparatus of claim 2, wherein the ball and socket joint comprises a ball disposed in a socket, wherein one of the nosecone proximal end portion and the nosecone distal end portion comprises the ball and the other of the nosecone proximal end portion and nosecone distal end portion comprises the socket.

4. The delivery apparatus of claim 3, wherein the nosecone proximal end portion comprises the socket and the nosecone distal end portion comprises the ball; and wherein the nosecone distal end portion comprises a tapered end portion, and wherein the tapered end portion is coupled to the ball.

5. The delivery apparatus of claim 4, wherein the tapered end portion has a cavity and the ball has a projection, and wherein the cavity is configured to receive the projection such that the tapered end portion is connected to the ball.

6. The delivery apparatus of claim 4, wherein the ball has a cavity and the tapered end portion has a projection, and wherein the cavity is configured to receive the projection such that the ball is connected to the tapered end portion.

7. The delivery apparatus of claim 3, wherein the nosecone distal end portion comprises the socket and the nosecone proximal end portion comprises the ball; and wherein the nosecone proximal end portion comprises a tapered end portion, wherein the tapered end portion is coupled to the ball.

8. The delivery apparatus of claim 1, wherein the nosecone proximal end portion has a ridge extending radially outwardly from an outer surface of the nosecone proximal end portion.

9. The delivery apparatus of claim 8, wherein the ridge extends circumferentially around the outer surface of the nosecone proximal end portion.

10. The delivery apparatus of claim 8, wherein the shaft comprises a first shaft and the delivery apparatus comprises a second shaft extending over the first shaft, the second shaft comprising a delivery capsule along a distal end section thereof, wherein the delivery capsule is configured to retain the implantable medical device in a radially collapsed state for delivery into a patient, and wherein a distal end section of the delivery capsule is sized to extend over the nosecone proximal end portion.

11. The delivery apparatus of claim 10, wherein the distal end section of the delivery capsule abuts the ridge while extending over the nosecone proximal end portion.

12. The delivery apparatus of claim 1, wherein the nosecone proximal end portion and the nosecone distal end portion are rotatably coupled to each other.

13. A delivery apparatus for an implantable medical device comprising:

a handle;

a shaft having a shaft proximal end portion and a shaft distal end portion, the shaft proximal end portion being coupled to the handle; and a nosecone coupled to the shaft distal end portion, wherein the nosecone comprises a nosecone proximal end portion and a nosecone distal end portion pivotably coupled to the nosecone proximal end portion by a ball and socket joint, the ball and socket joint comprising a ball disposed in a socket, wherein the nosecone proximal end portion comprises the socket and the nosecone distal end portion comprises the ball.

14. The delivery apparatus of claim 13, wherein the nosecone proximal end portion comprises a first lumen and the nosecone distal end portion comprises a second lumen, and wherein the first and second lumens are sized to receive a guidewire therethrough.

15. The delivery apparatus of claim 14, wherein the shaft distal end portion extends into the first lumen and the nosecone proximal end portion, and wherein the nosecone proximal end portion is adhered, welded, molded, or a combination thereof, to the shaft distal end portion.

16. The delivery apparatus of claim 14, wherein the first lumen comprises a first tapered lumen and the second lumen comprises a second tapered lumen, wherein the first tapered lumen and the second tapered lumen are proximate to and taper in opposite directions from one another; and wherein the first tapered lumen and the second tapered lumen are configured to permit the first lumen and the second lumen to be in constant communication as the nosecone proximal end portion and the nosecone distal end portion pivot relative to each other.

17. The delivery apparatus of claim 16, wherein the first lumen comprises a socket lumen, the first tapered lumen, and a shaft lumen, wherein the socket lumen is proximate to the first tapered lumen and the first tapered lumen is proximate to the shaft lumen; and wherein the socket lumen, the first tapered lumen, and the shaft lumen each comprise an inner diameter, wherein the inner diameter of the socket lumen is greater than or equal to the inner diameter of the first tapered lumen, and the inner diameter of the first tapered lumen is greater than or equal to the inner diameter of the shaft lumen.

18. The delivery apparatus of claim 16, wherein the second lumen comprises the second tapered lumen and a distal end lumen; and wherein the nosecone distal end portion comprises a tapered portion and the ball, and wherein the tapered portion comprises the distal end lumen and the ball comprises the second tapered lumen.

19. An implantable medical device delivery assembly comprising:

a delivery apparatus comprising a handle, a nosecone, a first shaft, and a second shaft extending over the first shaft, the first shaft comprising a first shaft distal end portion and a first shaft proximal end portion coupled to the handle, the second shaft comprising a delivery capsule along a second shaft distal end section thereof, and the nosecone comprising a nosecone proximal end portion and a nosecone distal end portion pivotably coupled to the nosecone proximal end portion; and an expandable implantable medical device mounted in a radially compressed configuration around the first shaft distal end portion and within the delivery capsule of the second shaft; and wherein the nosecone distal end portion and the nosecone proximal end portion are pivotably coupled by a ball and socket joint comprising a ball disposed in a socket, wherein the nosecone distal end portion comprises the ball and the nosecone proximal end portion comprises the socket, and wherein a distal end section of the delivery capsule is sized to extend over the nosecone proximal end portion.

20. The delivery assembly of claim 19, wherein the nosecone proximal end portion comprises an outer surface and an outer ridge, wherein the outer ridge extends outwardly from the outer surface and circumferentially around the nosecone proximal end portion, wherein the distal end section of the delivery capsule abuts the outer ridge while extending over the nosecone proximal end portion; and wherein the outer ridge comprises a first outer circumference and the distal end section of the delivery capsule comprises a second outer circumference, wherein the first outer circumference is equal to or substantially equal to the second outer circumference such that the outer ridge and the distal end section of the delivery capsule form a continuous outer surface extending from the nosecone to the handle.

* * * * *